(12) United States Patent
Bonnette et al.

(10) Patent No.: US 9,833,257 B2
(45) Date of Patent: *Dec. 5, 2017

(54) ENHANCED CROSS STREAM MECHANICAL THROMBECTOMY CATHETER

(71) Applicant: BOSTON SCIENTIFIC LIMITED, Hamilton (BM)

(72) Inventors: Michael J. Bonnette, Minneapolis, MN (US); Eric J. Thor, Arden Hills, MN (US); Michael Schrom, Forest Lake, MN (US); Debra M. Kozak, Forest Lake, MN (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 320 days.

This patent is subject to a terminal disclaimer.

(21) Appl. No.: 14/676,192

(22) Filed: Apr. 1, 2015

(65) Prior Publication Data

US 2015/0196317 A1    Jul. 16, 2015

Related U.S. Application Data

(60) Continuation of application No. 14/090,179, filed on Nov. 26, 2013, now Pat. No. 8,998,843, which is a
(Continued)

(51) Int. Cl.
   *A61B 17/3203*   (2006.01)
   *A61B 17/22*   (2006.01)
   *A61M 25/00*   (2006.01)

(52) U.S. Cl.
   CPC ........ *A61B 17/32037* (2013.01); *A61B 17/22* (2013.01); *A61M 25/0029* (2013.01);
   (Continued)

(58) Field of Classification Search
   CPC .............. A61B 17/32037; A61B 17/22; A61B 2017/22079; A61B 2017/22084;
   (Continued)

(56) References Cited

U.S. PATENT DOCUMENTS 1,902,418 A  3/1933  Pilgrim
1,904,241 A  4/1933  Kammerer
(Continued)

FOREIGN PATENT DOCUMENTS

DE   3421390 A1   12/1985
DE   3705339 A1    9/1988
(Continued)

OTHER PUBLICATIONS

"Dow Calibre® MEGARAD 2080 10 Polycarbonate, Gamma Radiation Resistant", Dow Chemical, 1 page, Nov. 14, 2008. http://www.matlab.com/search/datasheet_print. aspx?matguid=95e353321b09f039523274627el.

Primary Examiner — Manuel Mendez
(74) Attorney, Agent, or Firm — Seager, Tufte & Wickhem, LLP

(57) ABSTRACT

A thrombectomy catheter includes a catheter body having a catheter lumen. An outflow orifice is positioned along a catheter perimeter. A fluid jet emanator communicates with a high pressure tube. The fluid jet emanator includes at least one jet orifice for directing a fluid jet from the fluid jet emanator through the catheter lumen toward the outflow orifice. The fluid jet emanator provides a jet stream from the catheter body through the outflow orifice. The jet stream includes first and second stream portions. An entrainment fluid flow circuit includes at least the first stream portion, and the entrainment fluid flow circuit entrains particulate and macerates the particulate therein. An exhaust fluid flow path includes the second stream portion, and the exhaust fluid flow path draws entrained particulate from the entrain-
(Continued)

ment fluid flow circuit at a location exterior to the catheter body and directs it toward the catheter proximal portion.

20 Claims, 36 Drawing Sheets

Related U.S. Application Data division of application No. 13/453,498, filed on Apr. 23, 2012, now Pat. No. 8,597,238, which is a division of application No. 12/174,978, filed on Jul. 17, 2008, now Pat. No. 8,162,877, which is a division of application No. 11/009,720, filed on Dec. 10, 2004, now abandoned.

(52) U.S. Cl.
CPC ............. *A61B 2017/22079* (2013.01); *A61B 2017/22084* (2013.01); *A61B 2217/005* (2013.01); *A61M 25/005* (2013.01); *A61M 25/007* (2013.01); *A61M 25/0032* (2013.01); *A61M 25/0045* (2013.01); *A61M 2025/0034* (2013.01); *Y10T 29/49826* (2015.01)

(58) Field of Classification Search
CPC ........ A61B 2217/005; A61M 25/0029; A61M 25/0032; A61M 25/0045; A61M 25/005; A61M 25/007; A61M 2025/0034; Y10T 29/49826
USPC ... 604/28, 30, 500, 507–510, 22, 27, 35, 39, 604/40, 43, 73, 118, 131, 151, 158, 604/164.09, 164.13, 167.06, 275, 93.01; 606/159, 127, 128, 190, 191, 194
See application file for complete search history.

(56) References Cited

U.S. PATENT DOCUMENTS

| | | |
|---|---|---|
| 3,752,617 A | 8/1973 | Burlis et al. |
| 3,930,505 A | 1/1976 | Wallach |
| 4,033,331 A * | 7/1977 | Guss ............... A61M 25/0041 600/434 |
| 4,224,943 A | 9/1980 | Johnson et al. |
| 4,248,234 A | 2/1981 | Assenza et al. |
| 4,290,428 A | 9/1981 | Durand et al. |
| 4,328,811 A | 5/1982 | Fogarty |
| 4,385,635 A | 5/1983 | Ruiz |
| 4,582,181 A * | 4/1986 | Samson .......... A61M 25/09033 604/913 |
| 4,631,052 A | 12/1986 | Kensey |
| 4,636,346 A | 1/1987 | Gold et al. |
| 4,690,672 A | 9/1987 | Veltrup |
| 4,739,768 A | 4/1988 | Engelson |
| 4,747,405 A | 5/1988 | Leckrone |
| 4,781,186 A | 11/1988 | Simpson et al. |
| 4,782,834 A | 11/1988 | Maguire et al. |
| 4,790,813 A | 12/1988 | Kensey |
| 4,842,579 A | 6/1989 | Shiber |
| 4,861,336 A | 8/1989 | Helzel |
| 4,883,459 A | 11/1989 | Calderon |
| 4,888,146 A | 12/1989 | Dandeneau |
| 4,898,574 A | 2/1990 | Uchiyama et al. |
| 4,898,591 A | 2/1990 | Jang et al. |
| 4,902,276 A | 2/1990 | Zakko |
| 4,913,698 A | 4/1990 | Ito et al. |
| 4,935,017 A * | 6/1990 | Sylvanowicz .. A61M 25/09025 604/532 |
| 4,950,238 A | 8/1990 | Sullivan |
| 5,011,469 A | 4/1991 | Buckberg |
| 5,085,649 A | 2/1992 | Flynn |
| 5,086,842 A | 2/1992 | Cholet |
| 5,092,873 A | 3/1992 | Simpson et al. |
| 5,114,399 A | 5/1992 | Kovalcheck |
| 5,135,482 A | 8/1992 | Neracher |
| 5,163,431 A | 11/1992 | Griep |
| 5,215,614 A | 6/1993 | Wijkamp et al. |
| 5,221,270 A | 6/1993 | Parker |
| 5,234,416 A | 8/1993 | Macaulay et al. |
| 5,250,059 A | 10/1993 | Andreas et al. |
| 5,254,107 A | 10/1993 | Soltesz |
| 5,259,842 A | 11/1993 | Plechinger et al. |
| 5,273,526 A | 12/1993 | Dance et al. |
| 5,300,022 A | 4/1994 | Klapper et al. |
| 5,308,342 A | 5/1994 | Sepetka et al. |
| 5,318,518 A | 6/1994 | Plechinger et al. |
| 5,320,599 A | 6/1994 | Griep et al. |
| 5,324,285 A | 6/1994 | Cannon |
| 5,342,386 A | 8/1994 | Trotta |
| 5,358,485 A | 10/1994 | Vance et al. |
| 5,370,609 A | 12/1994 | Drasler et al. |
| 5,372,601 A | 12/1994 | Lary |
| 5,380,307 A | 1/1995 | Chee et al. |
| 5,395,315 A | 3/1995 | Griep |
| 5,399,164 A | 3/1995 | Snoke et al. |
| 5,425,723 A | 6/1995 | Wang |
| 5,453,088 A | 9/1995 | Boudewijn et al. |
| 5,456,674 A | 10/1995 | Bos et al. |
| 5,478,330 A | 12/1995 | Imran et al. |
| 5,496,267 A | 3/1996 | Drasler et al. |
| 5,496,294 A | 3/1996 | Hergenrother et al. |
| 5,499,973 A | 3/1996 | Saab |
| 5,531,685 A | 7/1996 | Hemmer et al. |
| 5,536,242 A | 7/1996 | Willard et al. |
| 5,542,924 A | 8/1996 | Snoke et al. |
| 5,554,114 A | 9/1996 | Wallace |
| 5,554,121 A | 9/1996 | Ainsworth et al. |
| 5,571,094 A | 11/1996 | Sirhan |
| 5,599,325 A | 2/1997 | Ju et al. |
| 5,624,397 A | 4/1997 | Snoke et al. |
| 5,634,897 A | 6/1997 | Dance et al. |
| 5,658,263 A | 8/1997 | Dang et al. |
| 5,662,622 A | 9/1997 | Gore et al. |
| 5,676,659 A | 10/1997 | McGurk |
| 5,681,336 A | 10/1997 | Clement et al. |
| 5,683,345 A | 11/1997 | Waksman et al. |
| 5,687,714 A | 11/1997 | Kolobow et al. |
| 5,702,439 A | 12/1997 | Euteneuer et al. |
| 5,704,926 A | 1/1998 | Sutton |
| 5,711,909 A | 1/1998 | Gore et al. |
| 5,713,849 A | 2/1998 | Bosma et al. |
| 5,785,675 A | 7/1998 | Drasler et al. |
| 5,792,167 A | 8/1998 | Kablik et al. |
| 5,902,266 A | 5/1999 | Leone et al. |
| 5,928,186 A | 7/1999 | Homsma et al. |
| 5,944,686 A | 8/1999 | Patterson et al. |
| 5,964,223 A | 10/1999 | Baran |
| 5,976,120 A | 11/1999 | Chow et al. |
| 5,989,210 A | 11/1999 | Morris et al. |
| 5,989,271 A | 11/1999 | Bonnette et al. |
| 5,997,558 A | 12/1999 | Nash |
| 6,001,078 A | 12/1999 | Reekers |
| 6,022,336 A | 2/2000 | Zadno-Azizi et al. |
| 6,024,729 A | 2/2000 | Dehdashtian et al. |
| 6,030,369 A | 2/2000 | Engelson et al. |
| 6,045,547 A | 4/2000 | Ren et al. |
| 6,063,069 A | 5/2000 | Cragg et al. |
| 6,096,001 A | 8/2000 | Drasler et al. |
| 6,117,150 A | 9/2000 | Pingleton et al. |
| 6,128,799 A | 10/2000 | Nagata et al. |
| 6,129,697 A | 10/2000 | Drasler et al. |
| 6,129,698 A | 10/2000 | Beck |
| 6,135,977 A | 10/2000 | Drasler et al. |
| 6,224,570 B1 | 5/2001 | Le et al. |
| 6,258,061 B1 | 7/2001 | Drasler et al. |
| 6,287,280 B1 | 9/2001 | Lampropoulos et al. |
| 6,331,176 B1 | 12/2001 | Becker et al. |
| 6,355,027 B1 | 3/2002 | Le et al. |
| 6,357,635 B1 | 3/2002 | Pagliaro et al. |
| 6,375,635 B1 | 4/2002 | Moutafis et al. |
| 6,409,863 B1 | 6/2002 | Prindle et al. |
| 6,414,420 B1 | 7/2002 | Suzuki |

(56) References Cited

U.S. PATENT DOCUMENTS

| | | |
|---|---|---|
| 6,420,205 B1 | 7/2002 | Sawai |
| 6,471,683 B2 | 10/2002 | Drasler et al. |
| 6,540,734 B1 | 4/2003 | Chiu et al. |
| 6,544,209 B1 | 4/2003 | Drasler et al. |
| 6,544,215 B1 | 4/2003 | Bencini et al. |
| 6,558,366 B1 | 5/2003 | Drasler et al. |
| 6,592,549 B2 | 7/2003 | Gerdts et al. |
| 6,635,070 B2 | 10/2003 | Leeflang et al. |
| 6,676,627 B1 | 1/2004 | Bonnette et al. |
| 6,676,637 B1 | 1/2004 | Bonnette et al. |
| 6,719,718 B2 | 4/2004 | Bonnette et al. |
| 6,755,803 B1 | 6/2004 | Le et al. |
| 6,764,483 B1 | 7/2004 | Bonnette et al. |
| 6,805,684 B2 | 10/2004 | Bonnette et al. |
| 6,875,193 B1 | 4/2005 | Bonnette et al. |
| 6,921,396 B1 | 7/2005 | Wilson et al. |
| 6,926,726 B2 | 8/2005 | Drasler et al. |
| 6,945,951 B1 | 9/2005 | Bonnette et al. |
| 6,964,657 B2 | 11/2005 | Cragg |
| 6,984,239 B1 | 1/2006 | Drasler et al. |
| 7,120,992 B2 | 10/2006 | He et al. |
| 7,179,291 B2 | 2/2007 | Rourke et al. |
| 7,226,433 B2 | 6/2007 | Bonnette et al. |
| 7,334,681 B2 | 2/2008 | Bonnette et al. |
| 7,572,244 B2 | 8/2009 | Weisel et al. |
| 7,879,022 B2 | 2/2011 | Bonnette et al. |
| 7,996,974 B2 | 8/2011 | Kozak et al. |
| 8,012,117 B2 | 9/2011 | Bonnette et al. |
| 8,597,238 B2 * | 12/2013 | Bonnette ................. A61B 17/22 604/93.01 |
| 2001/0051785 A1 * | 12/2001 | Bonnette ............. A61M 1/0084 604/35 |
| 2003/0127620 A1 | 7/2003 | Houde |
| 2004/0068248 A1 | 4/2004 | Mooney et al. |
| 2005/0059957 A1 | 3/2005 | Campbell et al. |
| 2006/0064123 A1 | 3/2006 | Bonnette et al. |

FOREIGN PATENT DOCUMENTS

| | | |
|---|---|---|
| EP | 232678 A2 | 8/1987 |
| EP | 251512 A1 | 1/1988 |
| EP | 232678 B1 | 4/1991 |
| EP | 528181 A1 | 2/1993 |
| EP | 1382366 A1 | 1/2004 |
| EP | 1382366 B1 | 11/2009 |
| WO | 9410917 A1 | 5/1994 |
| WO | 9905493 A1 | 2/1999 |
| WO | 0069348 A1 | 11/2000 |
| WO | 03000316 A1 | 1/2003 |
| WO | 2004064891 A2 | 8/2004 |

* cited by examiner

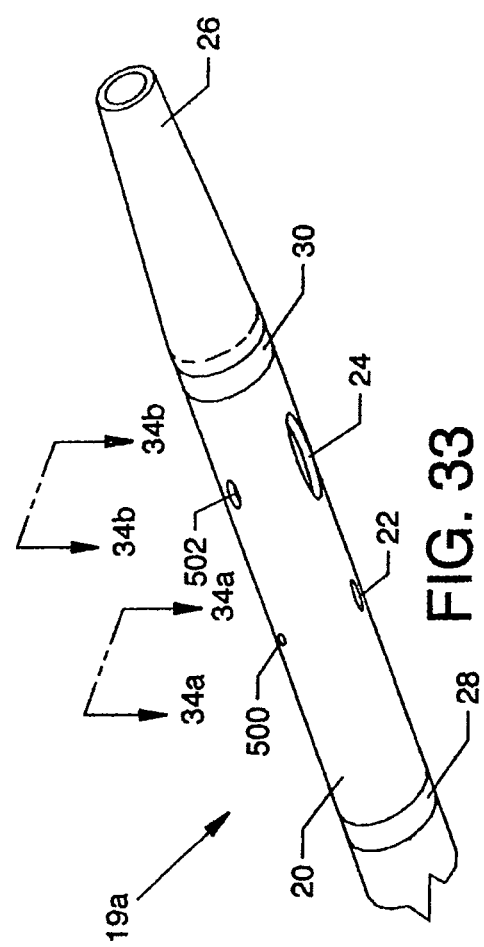

ENHANCED CROSS STREAM MECHANICAL THROMBECTOMY CATHETER

CROSS REFERENCE TO RELATED APPLICATIONS

This application is a Continuation Application of U.S. application Ser. No. 14/090,179, filed on Nov. 26, 2013, now U.S. Pat. No. 8,998,843, which is a divisional application of U.S. application Ser. No. 13/453,498, filed on Apr. 23, 2012, now U.S. Pat. No. 8,597,238, issued Dec. 3, 2013, which is a divisional of U.S. application Ser. No. 12/174,978, filed Jul. 17, 2008, now U.S. Pat. No. 8,162,877, issued Apr. 24, 2012, which is a divisional of U.S. application Ser. No. 11/009,720, filed on Dec. 10, 2004, which is abandoned, the contents of which are incorporated herein by reference. This application is related to U.S. application Ser. No. 10/455,096 filed Jun. 5, 2003, now U.S. Pat. No. 7,226,433, issued Jun. 5, 2007.

BACKGROUND

The present disclosure is for a thrombectomy catheter, and more particularly, relates to an enhanced cross stream mechanical thrombectomy catheter which accommodates interchanging of guidewires through rear loading of a guidewire, as well as loading of a guidewire in a conventional manner, and also provides for improved cross stream ablation at a thrombus site. The intended use of embodiments of this disclosure are for the detachment and removal of unwanted tissues, such as thrombus, from within biological conduits.

DESCRIPTION OF PRIOR ART

In current cross stream catheters, vessel damage by the multiple inflow/outflow cross stream catheters involves the vessel wall being sucked into the catheter at the side inlet orifice of the catheter. The high velocity fluid jets nick the vessel that is sucked into the catheter side inflow orifice. With the design described by the present disclosure, the vessel is pushed away by a single side outflow. The side of the catheter with no orifices is pushed against the vessel and consequently no damage results. This new mechanical thrombectomy design is referred to as the Enhanced Cross Stream Mechanical Thrombectomy Catheter with Backloading Manifold. The design employs one set of inflow and outflow orifices instead of the symmetrical multiple orifice configuration. Generally speaking, the cross sectional area of multiple sets of outflow/inflow orifices of prior art devices are newly combined into one set having a larger but equal cross sectional outflow/inflow orifice area to substantially increase and concentrate the cross stream action on one side of the device, thereby increasing the localized flow intensity considerably. In the present disclosure, all the flow is concentrated to one set of orifices and, in addition, the area for recirculation is maximized since it is designed to have a guidewire removed or pulled back out of the flow zone while using the device. Removing the guidewire from the orifice area of the catheter removes a substantial fluid restriction between the single side inflow orifice and the single side outflow orifice. In theory, removing this fluid restriction in all cross stream catheter designs should increase catheter performance. However, in the multiple orifice pair arrangements of the prior art, internal turbulent eddies consumed the area and an increase in performance often did not accompany the retraction of the guidewire. The single inflow orifice and outflow orifice arrangement of the present disclosure simplifies the internal fluid pathway, and as a result, marked flow increase associated with guidewire removal is consistent and dramatic. The guidewire does not need to be pulled out completely to achieve substantial improvements in efficacy. In fact, even with the guidewire in place, it is much more effective than similarly sized cross stream thrombectomy catheters. Furthermore, retracting the guidewire to free the orifice area of the catheter results in an even greater increase in catheter performance. This removal of the guidewire from the region of cross stream action (i.e., from the ID of the catheter) greatly increases the flow volume and reduces flow resistance in which recirculation can more readily occur, thereby enhancing function. Furthermore, in existing designs, a guidewire cannot be reliably retracted from the catheter without the potential of the guidewire exiting the inflow orifices when the physician pushes it back through the tip of the device. The orifices of existing designs can be made smaller, but then a greater number of orifices must be provided to maintain suitable flow, resulting in limiting cross stream action since the resistance though smaller orifices is greater. Therefore, a new arrangement was created to solve the problem. Specifically, the high pressure tube is placed in the center of the large inflow and outflow orifice effectively creating two smaller orifices with the least amount of resistance to flow with minimized manufacturing cost. The high pressure tube further directs the guidewire up and out of the tip of the distal portion of the catheter due to its geometry (i.e., rounded surface, thickness keeps wire away from wall, etc.). In summary, by utilizing one set of large inflow and outflow orifices with the ability to remove and replace the guidewire when desired, the cross stream ablation action can be concentrated and enhanced. Furthermore, the ability of removing and replacing the guidewire at the flexible tip or at the proximal end of the manifold leads to further enhancement. The user may replace the same guidewire or may utilize another guidewire of his choice ("guidewire swapping"). This ability is favorable to physicians since they want as many choices to perform their job to the best of their ability as possible (i.e., beneficial so they do not lose wire position, or that they may want a stiffer or more floppy guidewire to cross a tight stenosis or traverse tortuous anatomy). This enhancement is achieved through simple changes to the manifold, whereby an insert is included for guidewire routing.

There is yet another benefit to the asymmetrical design of the present disclosure at the catheter distal end where all of the jet stream outflow is directed from one side of the catheter distal end resulting in a powerful concentration of directed force and increased flow caused by removal or proximal retardation of the guidewire. Such benefit results in the distal portion of the catheter reactingly being directed and forced against the vessel wall opposite to the cross stream action. This movement beneficially keeps the inflow and outflow orifices away from the vessel wall. It has been shown that vessel contact with the inflow or outflow orifices (interior jets, suction, or a combination of both) can cause vessel damage in various degrees. Therefore, this "naked catheter" (i.e., there are other designs having cages or balloons which would keep the jet flow from contacting the walls, but this design uses active jet flow to position the device) design is very safe with respect to vessel wall damage.

Some alternatives of this design would use differently shaped orifices, such as slots, instead of holes, etc. Round, oval, elliptical, obround, tapered, slotted, rectangular, triangular, rounded corner, protruding, or multiple-radius configurations can be utilized for the inflow and/or outflow orifices, where the orifices could be shaped such as to direct the flow in a preferred direction.

The catheter body could also be shaped to maximize the effectiveness of the flow. Also, the body of the catheter at the distal end may include a 180.degree. reversal where the reversed distal end is utilized to aid in removing material from the vessel wall. The effectiveness of the catheter could also be increased by increasing the flow to the catheter tip, which would impart more energy to the system to do work.

There is an alternative design that is similar in principle to the first embodiments of the present disclosure but which uses a physical barrier to deflect the flow out the side outflow orifice. In the current cross stream designs, a static or slow moving column of fluid captures the energy from the high velocity fluid jets resulting in a recovered pressure near the side outflow orifices. This recovered pressure drives fluid out the side outflow orifices. The general principle is that the velocity fluid jets entrain surrounding fluid which enters the catheter from the side inlet orifices. This excess fluid must exit the catheter since the outflow rate of the catheter is balanced to equal the infused flow rate from a suction source, such as a pump. As a result, higher recovered pressure near the side outflow orifices, which generates the recirculating flow pattern at the catheter tip, is seen. There are a number of fluid mechanical inefficiencies associated with such a design. Primarily, the strong high velocity fluid jets end up traveling down past the side outflow orifices and eventually break up into large turbulent eddies. Guiding the flow out a side outflow orifice can preserve some of this energy rather than having it consumed by turbulence inside the catheter. Another alternative design is incorporated to implement waste flow removal by orienting most of the high velocity fluid jets forward and then deflecting them out the distal end of the catheter where a small number of proximal-facing high velocity fluid jets are utilized to drive outflow from the catheter. The other alternative is to apply a roller pump driven waste line to the guide catheter itself and use the roller pump negative pressure to evacuate the waste flow while the deflecting catheter is infusing flow into the patient.

SUMMARY

The general purpose of the present disclosure is to provide an enhanced cross stream mechanical thrombectomy catheter with backloading manifold. The enhanced cross stream mechanical thrombectomy catheter with backloading manifold is capable of traditional loading over the proximal end of a guidewire or accommodational backloading of the distal end of a guidewire, such as would be useful during an exchange of guidewires whether during or prior to a thrombectomy procedure. Loading of a guidewire through the proximal end of the backloading manifold is accommodated and facilitated by a self-sealing arrangement including a hemostatic nut and a seal at the proximal end of the backloading manifold and by a tubular insert centrally located along the interior of the tubular central body of the backloading manifold. The insert includes a proximally-facing beveled surface entrance leading to an integral and distally located central passageway which extends along the greater portion of the length of the insert where such proximally-facing beveled surface entrance is useful for directing and loading a guidewire (i.e., a proximally loaded and distally directed guidewire) which is first directed in a central direction by the proximally-facing beveled surface entrance followed by passage through the central passageway. The distal and truncated portion of the insert central passageway connects to the proximal end of a catheter tube composed of a braided catheter tube successively connected to a plastic smooth catheter tube leading to an integral flexible and tapered distal tip at the distal portion of the smooth catheter tube. The geometry of a fluid jet emanator and related structure near the distal tip of the smooth catheter tube assists and promotes passage of a guidewire passing in either direction through the fluid jet emanator and related structure.

Cross stream flow at the distal portion of the smooth catheter tube as produced by a fluid jet emanator is enhanced by the use of one outflow orifice and one inflow orifice, thereby allowing concentration and intensity of the cross stream flow to provide only one localized region of thrombus ablation. Such ablation flow creates forces urging the distal portion of the plastic catheter tube away from the ablation area (i.e., away from the cross stream flow) in order that the vascular walls are not blockingly engaged by the inflow orifice. Such distancing is also helpful in keeping the cross stream flow from being dangerously close to the vascular wall, thereby minimizing the possibility of vascular wall damage.

According to one or more embodiments of the present disclosure, there is provided an enhanced cross stream mechanical thrombectomy catheter with backloading manifold, including a backloading manifold having an exhaust branch and a high pressure connection branch extending from a tubular central body of the backloading manifold, a hemostatic nut threadingly secured to the proximal portion of a proximal cavity body of the backloading manifold, a tubular insert located in an insert cavity of the backloading manifold, a strain relief extending distally from a distal manifold extension of the backloading manifold, a catheter tube formed in part of a braided catheter tube being connected to the insert and extending through the strain relief and in part of a plastic smooth catheter tube successively connected to the braided catheter tube, an inflow and an outflow orifice spaced longitudinally along one side of and located near the proximal end of the plastic smooth catheter tube, an integral flexible tip at the distal end of the plastic smooth catheter tube, and a high pressure tube extending through the high pressure connection branch, through portions of the backloading manifold, partially through the insert, and through the catheter tube composed of the braided catheter tube and plastic smooth catheter tube to terminate as a fluid jet emanator near the distal portion of the plastic smooth catheter tube where such termination is distal of the inflow and the outflow orifices, as well as other components described herein.

One significant aspect and feature of embodiments of the present disclosure include an enhanced cross stream mechanical thrombectomy catheter with backloading manifold with enhanced efficacy due to concentration of all the flow to one set of inflow and outflow orifices with a guidewire in place.

Another significant aspect and feature of embodiments of the present disclosure include an enhanced cross stream mechanical thrombectomy catheter with backloading manifold with even greater enhanced efficacy due to concentration of all the flow to one set of inflow and outflow orifices with the removal, retarding or other positioning of a guidewire.

Yet another significant aspect and feature of embodiments of the present disclosure include an enhanced cross stream mechanical thrombectomy catheter with backloading manifold that utilizes the position of the high pressure tube in relation to the outflow and inflow orifices to enable a guidewire to move freely in and out of the catheter tube without going out one of the orifices.

Still another significant aspect and feature of embodiments of the present disclosure include an enhanced cross stream mechanical thrombectomy catheter with backloading manifold that has a specially designed insert that allows a guidewire to be completely removed and replaced or exchanged for another desired guidewire.

Another significant aspect and feature of embodiments of the present disclosure include an enhanced cross stream mechanical thrombectomy catheter with backloading manifold that can be safer than other cross stream designs since the outflow orifice flow pushes the distal catheter end containing the inflow orifice and the outflow orifice away from the vessel wall (the region were damage can occur), thereby minimizing the possibility of blood vessel wall ingestion by the inflow orifice.

Another significant aspect and feature of embodiments of the present disclosure include an enhanced cross stream mechanical thrombectomy catheter with backloading manifold that employs many of the above significant aspects and features plus additionally including a catheter having a reversed distal end incorporated to intimately contact and remove grumous material from a vessel wall by direct abrading contact and by cross stream flow ablation.

Another significant aspect and feature of embodiments of the present disclosure include an enhanced cross stream mechanical thrombectomy catheter with backloading manifold that employs many of the above significant aspects and features and has inflow and outflow orifices shaped or sized to give optimal flow direction or performance.

Another significant aspect and feature of embodiments of the present disclosure include an enhanced cross stream mechanical thrombectomy catheter with backloading manifold that employs many of the above significant aspects and features and wherein the efficacy can be increased by increasing flow to the jet orifices (i.e., currently 60 cc of fluid delivered per minute . . . increased to 100 cc/min).

Another significant aspect and feature of embodiments of the present disclosure include an enhanced cross stream mechanical thrombectomy catheter with backloading manifold that employs deflection for concentrating and redirecting high velocity fluid jets to form cross stream jets with or without exhaust as an alternative design.

Another significant aspect and feature of embodiments of the present disclosure include an enhanced cross stream mechanical thrombectomy catheter with backloading manifold that can operate in a pressure range of 100 to 20,000 psi.

Yet another significant aspect and feature of embodiments of the present disclosure are the use of additional outflow orifices and inflow orifices in angular off-center opposition to the main outflow orifice and the inflow orifice.

Having thus described embodiments of the present disclosure and set forth significant aspects and features of embodiments of the present disclosure, it is the principal object of the present disclosure to provide an enhanced cross stream mechanical thrombectomy catheter with backloading manifold.

BRIEF DESCRIPTION OF THE DRAWINGS

Other objects of the present disclosure and many of the attendant advantages of embodiments of the present disclosure will be readily appreciated as the same becomes better understood by reference to the following detailed description when considered in connection with the accompanying drawings, in which like reference numerals designate like parts throughout the figures thereof and wherein:

FIG. 33, a fifth alternative embodiment, is a view of the distal portion of an alternatively provided smooth catheter tube assembly incorporating the components of the smooth catheter tube assembly shown in the first embodiment and including additional outflow orifices and inflow orifices in angular off-center opposition to the main outflow orifice and the main inflow orifice;

DETAILED DESCRIPTION OF THE PREFERRED EMBODIMENTS

Figure 1:
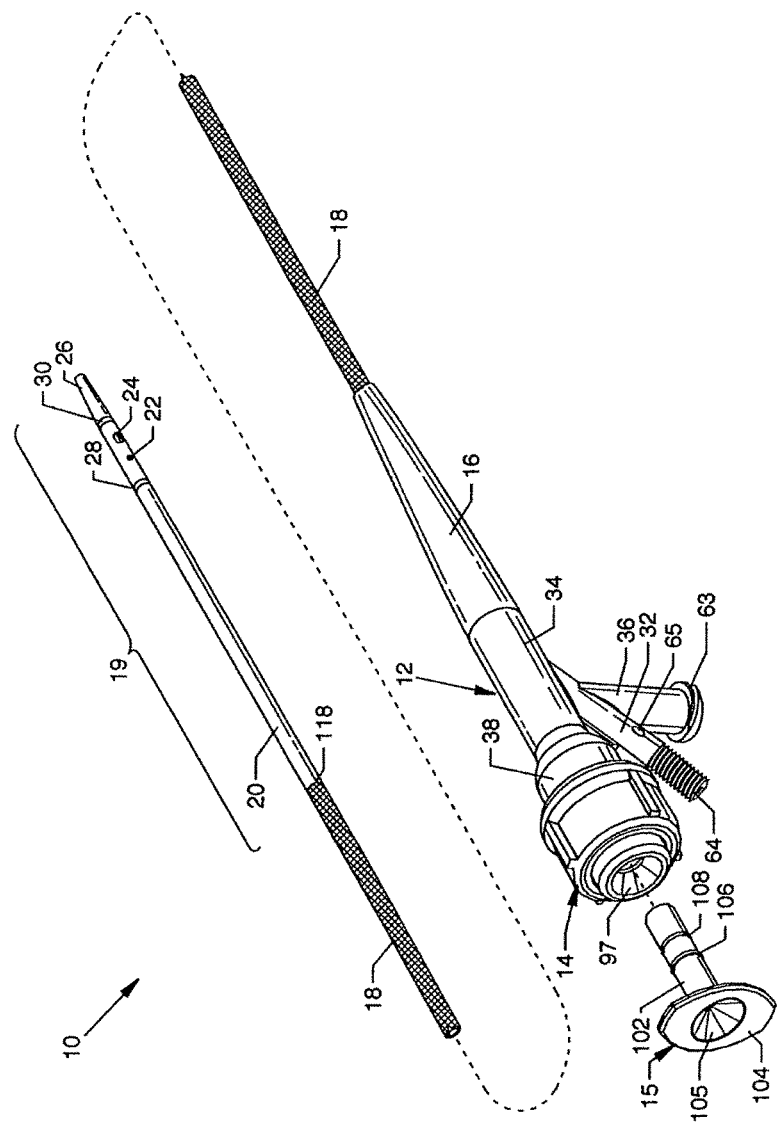
FIG. 1 is an isometric view of an enhanced cross stream mechanical thrombectomy catheter with backloading manifold, the present disclosure.

FIG. 1 is an isometric view of an enhanced cross stream mechanical thrombectomy catheter with backloading manifold 10. Externally visible major components of an embodiment of the present disclosure include a centrally located backloading manifold 12, a hemostatic nut 14 threadingly secured to the backloading manifold 12, an introducer 15, a flexible and tapered strain relief 16 connected to and extending from the backloading manifold 12, a catheter tube composed of a braided catheter tube 18 of flexible or semi-flexible material, preferably polyimide or other such suitable composition, connected to the backloading manifold 12 and extending through the tapered and flexible strain relief 16 and a smooth catheter tube assembly 19 having a smooth catheter tube 20 of plastic composition connected to and extending distally from the braided catheter tube 18, and an outflow orifice 22 and an inflow orifice 24 located in longitudinal alignment along an imaginary line at the distal portion of the smooth catheter tube 20 near a flexible tapered tip 26 located distally at the end of the smooth catheter tube 20. The components of the smooth catheter tube assembly 19 are depicted fully in FIGS. 2 and 3. For illustration purposes, the outflow orifice 22 and the inflow orifice 24, which extend through the smooth catheter tube 20, are shown on the side of the smooth catheter tube 20, but can be located along any imaginary line extending longitudinally along a distal surface of the smooth catheter tube 20, such as is shown in FIGS. 3, 7, 10 and 11. Normally, the catheter tube 18 is formed as a braided construction for strength, as shown, but it can be effectively formed in other ways: for example, by using reinforcing components such as fibers, wound strands, rings, wraps, or combinations thereof. Other externally visible major components include a radiopaque marker band 28 located on the smooth catheter tube 20 in close proximity to and proximal to the outflow orifice 22, a radiopaque marker band 30 located on the smooth catheter tube 20 in close proximity to and distal to the inflow orifice 24, a high pressure connection branch 32 extending from the central body 34 of the backloading manifold 12, an exhaust branch 36 extending from the junction of the central body 34 of the backloading manifold 12 and the high pressure connection branch 32, and a high pressure connector 64 engaging with and extending from the high pressure connection branch 32 of the backloading manifold 12. An orifice 65 located in the high pressure connection branch 32 allows for the introduction of adhesive 61 (FIG. 5) to secure the high pressure connector 64 in the high pressure connection branch 32.

Figure 2:
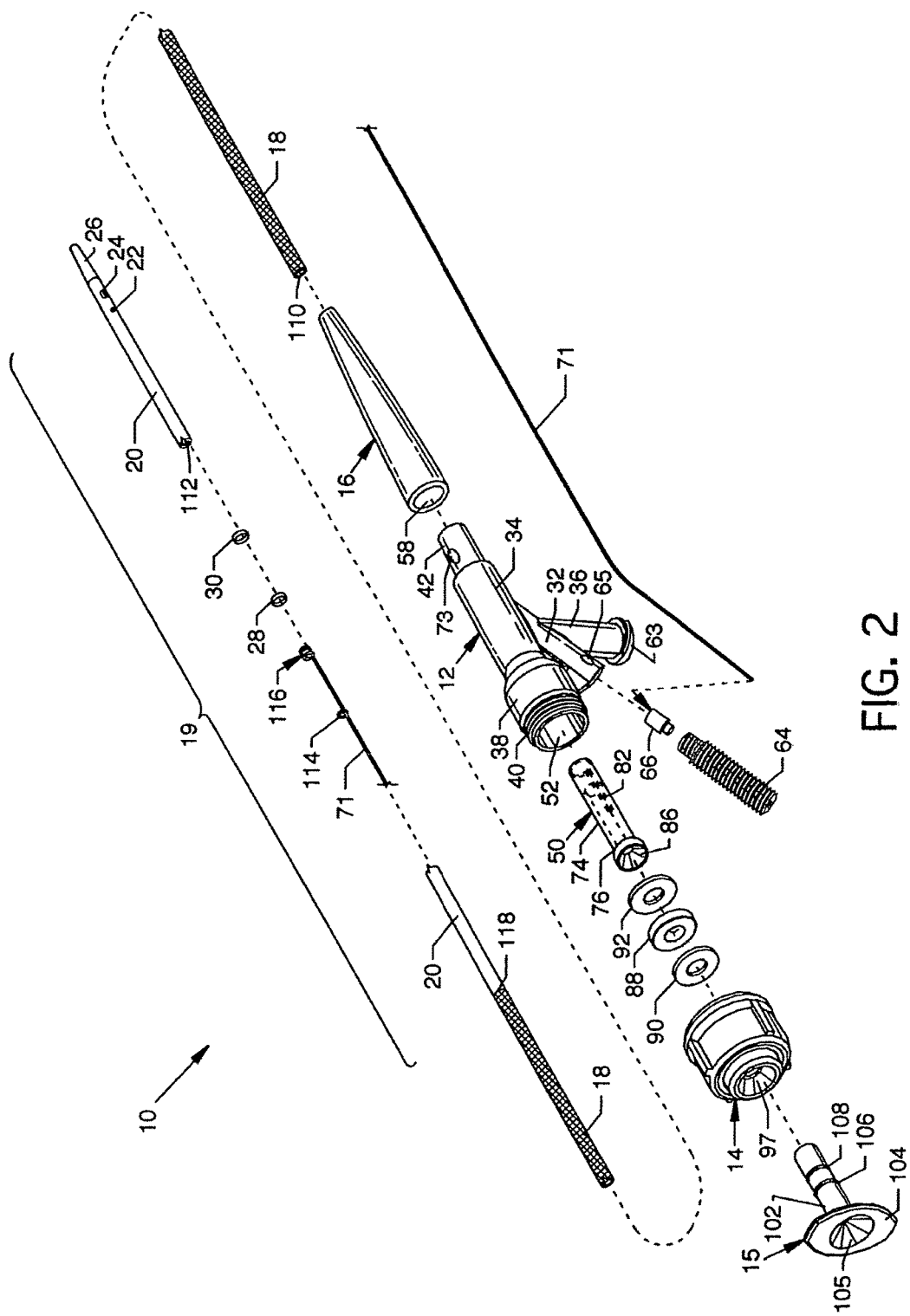
FIG. 2 is an isometric exploded view of the enhanced cross stream mechanical thrombectomy catheter with backloading manifold.
Figure 3:
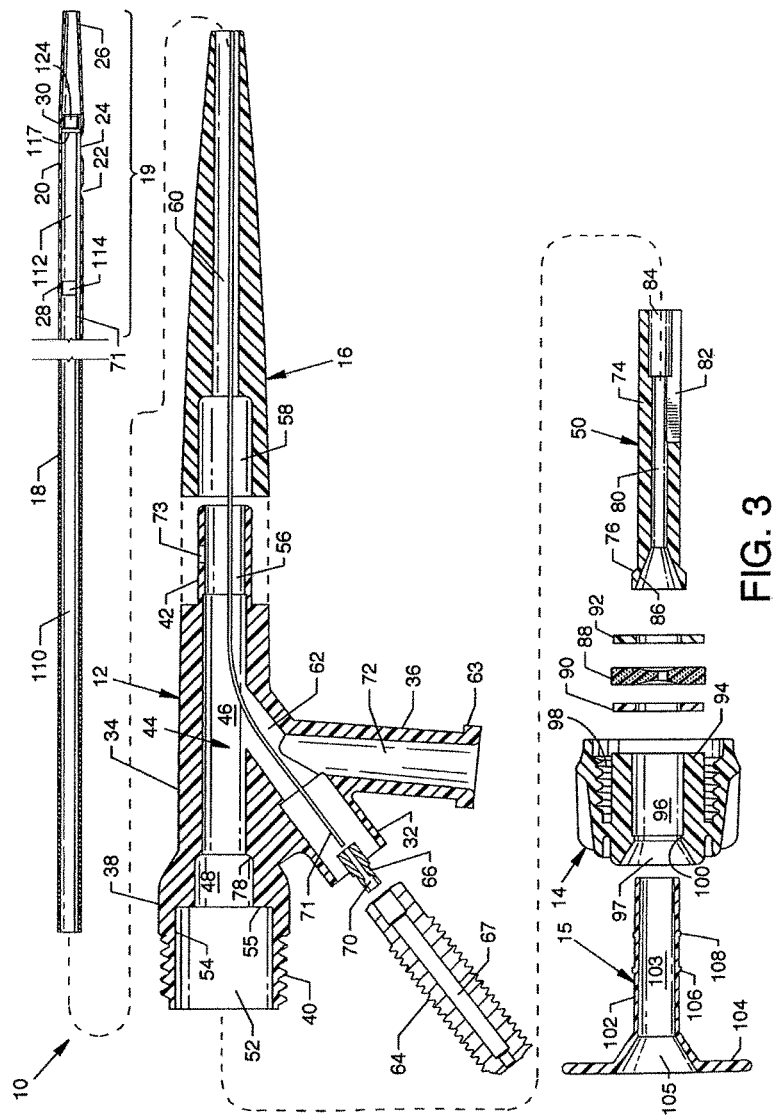
FIG. 3 is an exploded cross section side view of the components of the enhanced cross stream mechanical thrombectomy catheter with backloading manifold.

FIG. 2 is an isometric exploded view of the enhanced cross stream mechanical thrombectomy catheter with backloading manifold 10, and FIG. 3 is an exploded cross section side view of the components of the enhanced cross stream mechanical thrombectomy catheter with backloading manifold 10.

The backloading manifold 12 includes the central body 34 which is tubular and has on one end a proximally located cavity body 38 including an externally located threaded surface 40 and on the other end a distally located tubular manifold extension 42, including an orifice 41 which is utilized to introduce adhesive 43 (FIG. 5) to secure the proximal end of the braided catheter tube 18 to the distal manifold cavity 56. A multi-radius insert cavity 44 is continuously co-located within the central body 34 and a portion of the adjacent cavity body 38. The multi-radius insert cavity 44 is comprised of an elongated distal insert cavity portion 46 located coaxially within the central body 34 adjacent to and connecting to a proximal insert cavity portion 48 located coaxial to the cavity body 38 in continuous fashion. The insert cavity 44 accommodates an insert 50. A proximal manifold cavity 52 is located coaxially within the cavity body 38 and is continuous with and proximal to the proximal insert cavity portion 48 and an annular cavity wall 54 and an annular and planar surface 55 located between the annular cavity wall 54 and the proximal insert cavity portion 48. The manifold extension 42 extending distally from the distal end of the backloading manifold 12 includes an inwardly located distal manifold cavity 56 for passage of the proximal end of the braided catheter tube 18. The exterior of the manifold extension 42 accommodates the strain relief 16. The strain relief 16 is of flexible construction and includes a proximally located strain relief mounting cavity 58 connected to a passageway 60 both of which extend along the longitudinal axis of the strain relief 16. The strain relief mounting cavity 58 accommodates the manifold extension 42, which can be appropriately secured therein, such as by adhesive or mechanical interference. The high pressure connection branch 32 includes a high pressure connection branch passageway 62 intersecting and communicating with the distal insert cavity portion 46 of the insert cavity 44, as well as offering accommodation of the threaded high pressure connector 64. A ferrule 66 having a central bore 70 is accommodated by the lumen 67 of the high pressure connector 64. One end of a high pressure tube 71 is accommodated by and sealingly secured to the central bore 70 of the ferrule 66, such as by a weldment or mechanical interference. An exhaust branch passageway 72 central to the exhaust branch 36 communicates with the high pressure connection branch passageway 62 and with the distal insert cavity portion 46 of the insert cavity 44. The exhaust branch 36 has a threaded surface 63 at its end for attaching to suction apparatus. The entire insert 50 is accommodated by the insert cavity 44 where the distal insert cavity portion 46 and the proximal insert cavity portion 48 fittingly accommodate separate geometric configurations of the insert 50.

Figure 4:
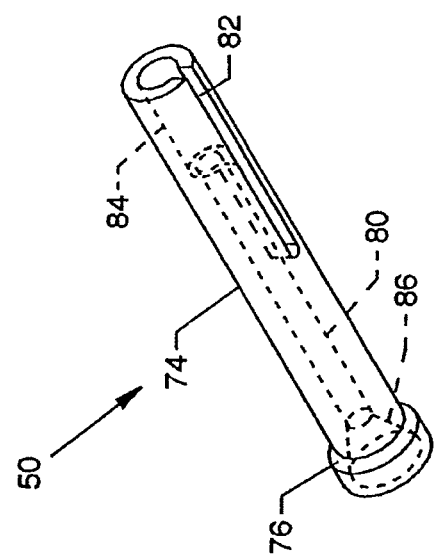
FIG. 4 is an isometric view of the insert showing an elongated slot extending through the main body.
Figure 5:
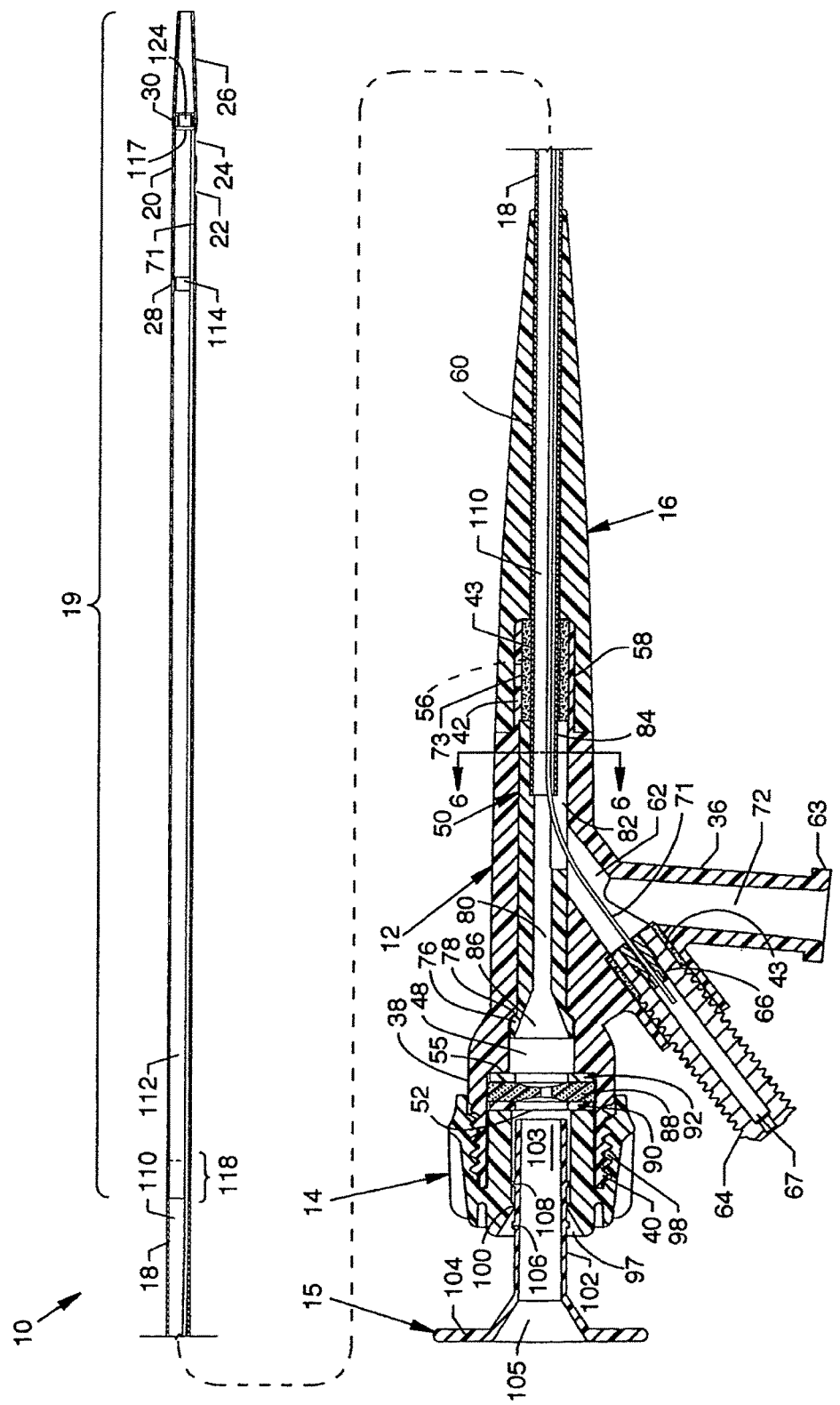
FIG. 5 is a cross section view of the assembled elements of FIG. 3.

As also shown in the isometric view of FIG. 4, the insert 50 includes a tubular main body 74 having a proximally located shoulder 76 which can be tapered or of other suitable geometric configuration. The shoulder 76 engages an annular transition stop surface 78 (FIG. 3) between the proximal insert cavity portion 48 and the distal insert cavity portion 46. One end of a central passageway 80 truncatingly intersects an elongated slot 82; and such central passageway also intersects a bore 84 which is also truncated by intersecting the elongated slot 82, i.e., the central passageway 80 adjoins bore 84 and each is truncated by intersection with the elongated slot 82. The elongated slot 82 extends through the main body 74 to intersect and align to a portion of the longitudinal axis of the insert 50. The elongated slot 82 accommodates passage of the high pressure tube 71, as shown in FIG. 5. The central passageway 80 has a proximally located beveled surface entrance 86 resembling a cone. The beveled surface entrance 86 is utilized for guidance and alignment for backloading of a guidewire through the backloading manifold 12, as later described in detail.

Beneficial to an embodiment of the present disclosure is the use of a self-sealing hemostatic valve 88, flanking washers 90 and 92, and an introducer 15 which are related to a patent application entitled "Thrombectomy Catheter Device Having a Self-Sealing Hemostatic Valve," U.S. Pat. No. 7,226,433. The self-sealing hemostatic valve 88, which is slightly oversized with respect to the proximal manifold cavity 52, and the washers 90 and 92 are aligned in and housed in the proximal manifold cavity 52 at one end of the backloading manifold 12. The hemostatic nut 14 includes a centrally located cylindrical boss 94, a central passageway 96 having a beveled surface entrance 97 extending through and in part forming the cylindrical boss 94, and internal threads 98. The internal threads 98 of the hemostatic nut 14 can be made to engage the threaded surface 40 of the backloading manifold 12, whereby the cylindrical boss 94 is brought to bear against the washer 90 to resultantly bring pressure to bear as required against the self-sealing hemostatic valve 88 and washer 92. The washers 90 and 92 and the self-sealing hemostatic valve 88 are captured in the proximal manifold cavity 52 by threaded engagement of the hemostatic nut 14 to the cavity body 38 of the backloading manifold 12. Also included in the hemostatic nut 14 is an annular lip 100 which can be utilized for snap engagement of particular styles or types of introducers, as required, such as introducer 15 provided to aid in accommodation of a guidewire in either direction and to provide for venting for the interior of the backloading manifold 12. The introducer 15 includes a centrally located shaft 102 with a central passageway 103 having a beveled surface entrance 105, an actuating handle 104, and rings 106 and 108 about the shaft 102. Also shown in FIG. 3 is a lumen 110 central to the braided catheter tube 18 which joiningly connects to and communicates with a lumen 112 central to the smooth catheter tube 20. A circular support ring 114 is suitably attached to the high pressure tube 71, such as by a weldment, and is located within the smooth catheter tube 20 in supporting alignment with the radiopaque marker band 28. A fluid jet emanator 116 including terminated loop 117 at the distal end of the high pressure tube 71 and a circular support ring 124 is located distal of the inflow orifice 24 within the distal end of the smooth catheter tube 20 in alignment with the radiopaque marker band 30, as later shown in detail in FIG. 10. The circular support rings 114 and 124 together with the respective associated radiopaque marker bands 28 and 30 constitute means for retaining the high pressure tube 71 in alignment with the catheter tube composed of braided catheter tube 18 and the smooth catheter tube 20.

FIG. 4 is an isometric view of the insert 50 showing the elongated slot 82 extending through the main body 74 in intersection with the central passageway 80 and the bore 84. The elongated slot 82 is beneficial for accommodation of the high pressure tube 71, as well as for communication between the combined lumens 110 and 112 of the braided catheter tube 18 and the smooth catheter tube 20, respectively, and the high pressure connection branch passageway 62 and the exhaust branch passageway 72, as shown in FIG. 5.

FIG. 5 is a cross section view of the assembled elements of FIG. 3. Particularly shown is the relationship of the high pressure tube 71, the insert 50, the lumen 110 of the braided catheter tube 18, and the proximal end of the braided catheter tube 18. The proximal portion of the high pressure tube 71 extends distally from the ferrule 66 through the high pressure connection branch passageway 62, through the elongated slot 82 of the insert 50 while traversing the distal portion of the central passageway 80 en route to and into the lumen 110 of the braided catheter tube 18, and thence along the lumen 110 and into the lumen 112 of the smooth catheter tube 20 to terminate as part of the fluid jet emanator 116 shown adjacent to the flexible tapered tip 26 at the distal end of the smooth catheter tube 20. In addition to providing a passage for the high pressure tube 71, the elongated slot 82 allows communication between the lumen 110 of the braided catheter tube 18 and the lumen 112 of the smooth catheter tube 20, collectively, and the high pressure connection branch passageway 62 and the exhaust branch passageway 72 for evacuation of effluence therefrom. Also shown is the junction 118 between the smooth catheter tube 20 and the braided catheter tube 18, such junction being suitably effected to provide for a smooth and continuous coupling of the smooth catheter tube 20 and the braided catheter tube 18.

Figure 6:
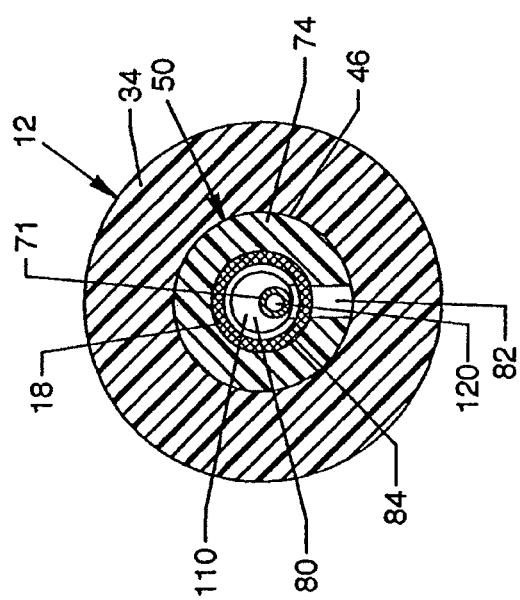
FIG. 6 is a cross section view of the enhanced cross stream mechanical thrombectomy catheter with backloading manifold along line 6-6 of FIG. 5.

FIG. 6 is a cross section view of the enhanced cross stream mechanical thrombectomy catheter with backloading manifold 10 along line 6-6 of FIG. 5. Shown in particular is the elongated slot 82 through which the high pressure tube 71 passes (passage of high pressure tube 71 not shown) and through which communication takes place between the lumen 110 of the braided catheter tube 18 and the high pressure connection branch passageway 62 and the exhaust branch passageway 72. Also shown is a lumen 120 central to the high pressure tube 71.

Figure 7:
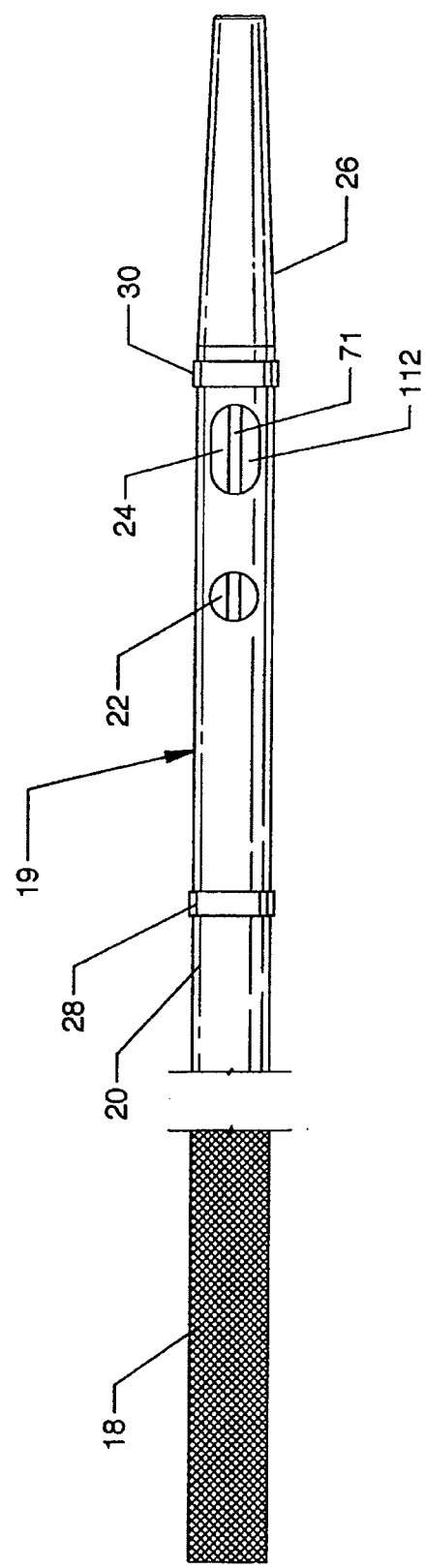
FIG. 7 is a bottom view of the distal end of the enhanced cross stream mechanical thrombectomy catheter with backloading manifold showing the smooth catheter tube, the outflow orifice, and the inflow orifice, as well as the high pressure tube visible through the outflow orifice and the inflow orifice.

FIG. 7 is a bottom view of the distal end of the enhanced cross stream mechanical thrombectomy catheter with backloading manifold 10 showing the smooth catheter tube 20 and the outflow orifice 22 and the inflow orifice 24, as well as the high pressure tube 71 visible through the outflow orifice 22 and the inflow orifice 24.

Figure 8:
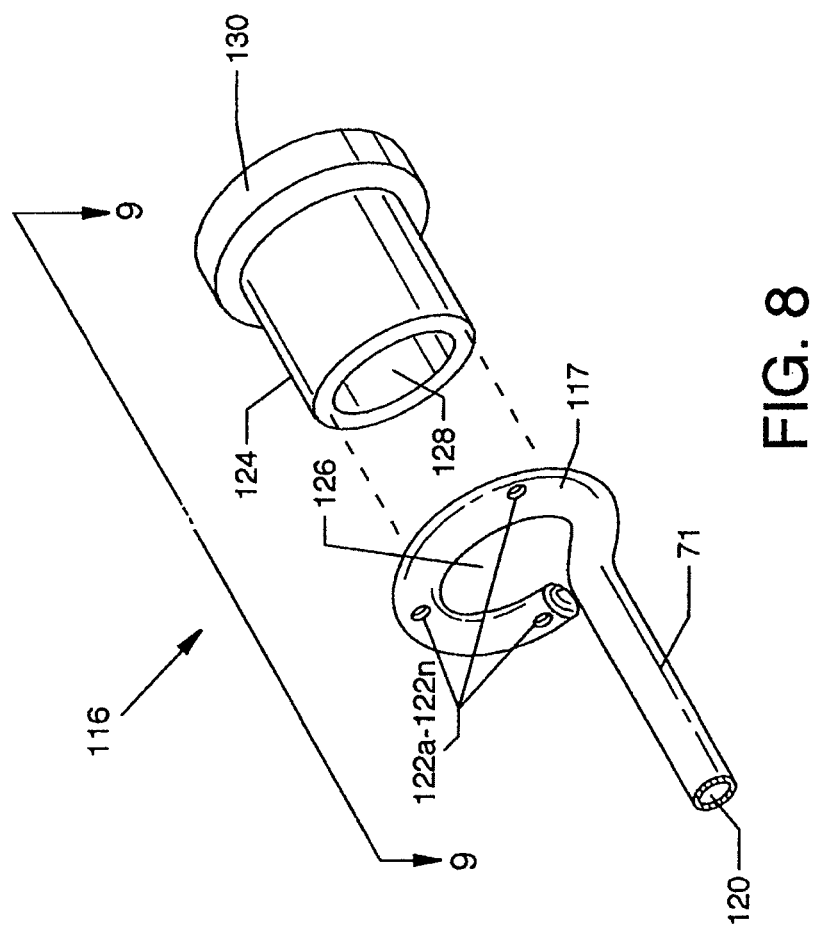
FIG. 8 is an isometric view of the fluid jet emanator.
Figure 9:
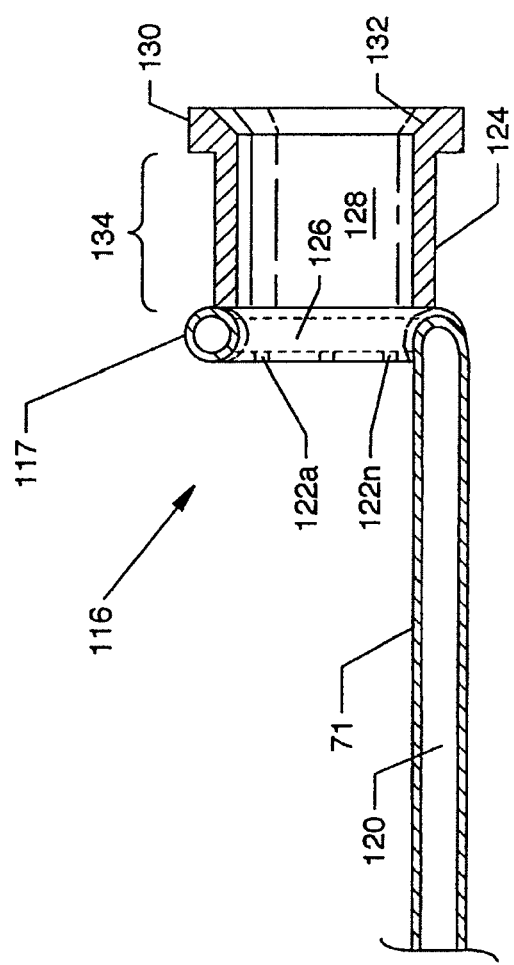
FIG. 9 is a side view in cross section along line 9-9 of FIG. 8 of the fluid jet emanator.
Figure 10:
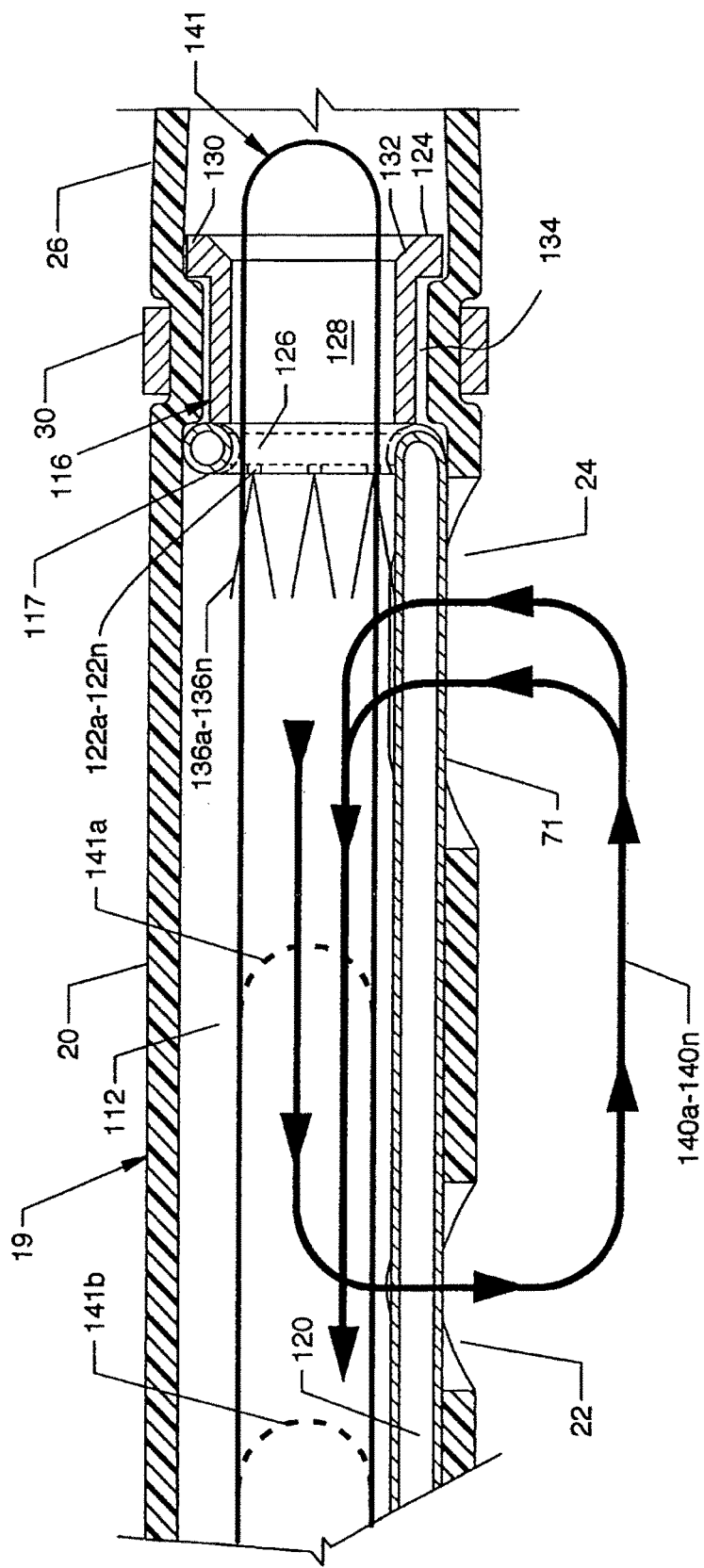
FIG. 10 is a side view in cross section illustrating the elements of FIG. 9 secured in the distal portion of the smooth catheter tube by a radiopaque marker band, as well as showing the cross stream flow.

FIG. 8 is an isometric view and FIG. 9 is a side view in cross section along line 9-9 of FIG. 8 of the fluid jet emanator 116. The fluid jet emanator 116 includes a terminated loop 117 at the distal end of the high pressure tube 71 and includes the support ring 124. The terminated loop 117 includes a plurality of proximally directed jet orifices 122a-122n. The support ring 124 suitably secures to the distal surface of the terminated loop 117 such as by a weldment. A center void 126 of the terminated loop 117 allows for passage of a guidewire or other suitable devices. The support ring 124, a tubular device, includes a central passageway 128 corresponding in use to that of the center void 126 of the terminated loop 117 for passage of a guidewire or other suitable devices. A distally located annular shoulder 130 on the support ring 124 allows for the inclusion of a beveled annular surface 132 juxtaposing the central passageway 128 to aid in the guided accommodation of a guidewire or other suitable device at the distal portion of the central passageway 128. A wide annular groove 134 is formed between the annular shoulder 130 and the distally facing surface of the terminated loop 117 and the smaller radiused body of the support ring 124. The wide annular groove 134 is utilized to secure the fluid jet emanator 116 at a suitable location in the distal portion of the smooth catheter tube 20, as shown in FIG. 10.

Mode of Operation

The mode of operation of the enhanced cross stream mechanical thrombectomy catheter with backloading manifold 10 is explained with reference to FIGS. 10, 11 and 12. FIG. 10 illustrates the elements of FIG. 9 secured in the distal portion of the smooth catheter tube 20 by the radiopaque marker band 30 which forces an annular portion of the smooth catheter tube 20 into the wide annular groove 134 formed by the support ring 124 and the terminated loop 117 of the fluid jet emanator 116. High velocity fluid jets 136a-136n are shown emanating proximally from the plurality of jet orifices 122a-122n into the lumen 112 of the smooth catheter tube 20 for subsequent creation of and culminating in cross stream jets 140a-140n, as depicted by heavy lines, which flow from the outflow orifice 22 and return through the inflow orifice 24 for ablative action with thrombus material and for maceration of foreign material in concert with the high velocity fluid jets 136a-136n and or for exhausting proximally with the flow within the distal portion of the smooth catheter tube 20. A guidewire 141 is also shown in see-through depiction, including alternate guidewire end positions 141a and 141b designated by dashed lines, where the guidewire 141 extends along the lumen 112 of the smooth catheter tube 20, through the center void 126 of the terminated loop 117, and through the central passageway 128 of the support ring 124 into the proximal portion of the flexible tapered tip 26. Guidewire 141 can be advanced beyond the flexible tapered tip 26 of the smooth catheter tube 20 such as during positioning of the catheter within the blood vessel or other body cavity, and then withdrawn to alternate guidewire end positions 141a and 141b, or other positions within the smooth catheter tube 20, or withdrawn completely from the smooth catheter tube 20. An advantage of an embodiment of the present disclosure is that the guidewire 141 can be introduced by a front loading approach or by a backloading approach and, therefore, can be removed and reintroduced or can be replaced by a different guidewire.

Figure 11:
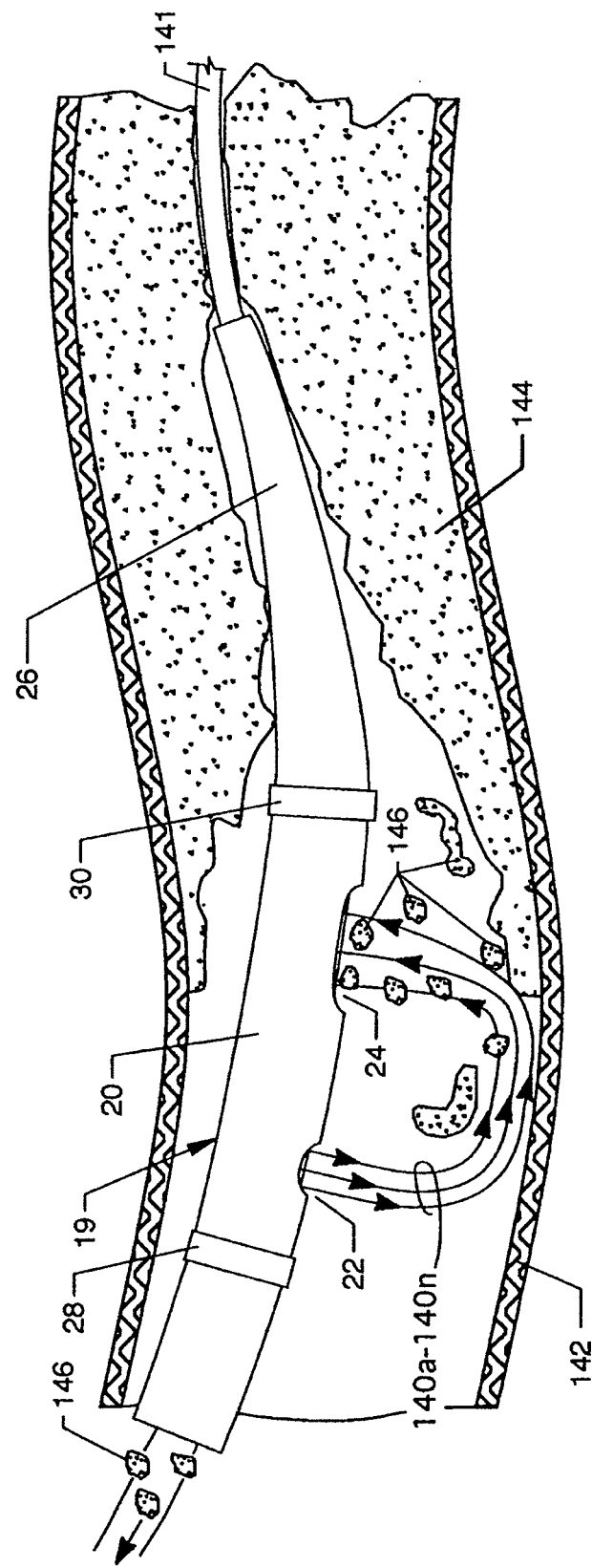
FIG. 11 is a side view of the distal region of the enhanced cross stream mechanical thrombectomy catheter with backloading manifold showing the distal end of a smooth catheter tube assembly positioned in a blood vessel (shown in cross section) at a site of a thrombotic deposit or lesion.

FIG. 11 is a side view of the distal region of the enhanced cross stream mechanical thrombectomy catheter with backloading manifold 10 showing in particular the distal end of the smooth catheter tube assembly 19 positioned in a blood vessel 142 (shown in cross section) at a site of a thrombotic deposit or lesion 144. While FIG. 11 depicts the smooth catheter tube assembly 19 as being in a blood vessel in particular, it is to be understood that it is not limited to use in a blood vessel but has utility with respect to any body cavity in general. High velocity fluid jets 136a-136n (shown in FIG. 10) of saline or other suitable solution are emanated or emitted in a proximal direction from the fluid jet emanator 116 into the smooth catheter tube 20 and pass through the outflow orifice 22 creating cross stream jets 140a-140n directed toward the wall of the blood vessel 142 having thrombotic deposits or lesions 144 and thence are influenced by the low pressure at the inflow orifice 24 to cause the cross stream jets 140a-140n to be directed distally substantially parallel to the central axis of the blood vessel 142 to impinge and break up thrombotic deposits or lesions 144 and to, by entrainment, urge and carry along the dislodged and ablated thrombotic particulates 146 of the thrombotic deposits or lesions 144 through the inflow orifice 24, a relatively low pressure region, and into the lumen 112, which functions as a recycling maceration lumen or chamber and also as an exhaust lumen. The entrainment through the inflow orifice 24 is based on entrainment by the high velocity fluid jets 136a-136n. The outflow is driven by internal pressure which is created by the high velocity fluid jets 136a-136n and the fluid entrained through the inflow orifice 24. The enhanced clot removal is enabled because of the recirculation pattern established between inflow and outflow orifices 22 and 24, which creates a flow field that maximizes drag force on wall-adhered thrombus, and because of impingement of the cross stream jets 140a-140n. The cross stream jets 140a-140n, whilst being forcefully directed outwardly and toward the wall of the blood vessel 142, by opposite reaction urge the distal portion of the smooth catheter tube 20 in the direction opposite the outward flow direction and away from the impingement area of the cross stream jets 140a-140n with the immediate thrombotic deposit or lesion 144 and/or the wall of the blood vessel 142, thus distancing the highly concentrated high velocity cross stream jets 140a-140n from the immediate thrombotic deposit or lesion 144 and/or the wall of the blood vessel 142 and thereby minimizing potential blood vessel wall damage. The cross stream jets 140a-140n traversing between the outflow orifice 22 and the inflow orifice 24 combine to offer an enhanced broad cross section ablation area, such area having a breadth substantially larger and having more concentrated force than prior art devices using multiple inflow and outflow orifices where cross streams are of diminished force and breadth. Having a concentrated flow combining cross stream jets 140a-140n offers selective and directed ablation to take place. Prior art devices using multiple inflow and outflow orifices and having multiple flow areas generate cross streams which are equally weak in all directions, as the flow force is divided between the multiple flow streams, whereby ablation forces cannot be concentrated where desired. The distal end of the smooth catheter tube 20 can be rotated axially to direct the cross stream jets 140a-140n about a longitudinal axis to have 360.degree. coverage or can be rotated axially to offer coverage partially about the longitudinal axis, as required.

The placement of the guidewire 141 within or the removal of the guidewire 141 from the enhanced cross stream mechanical thrombectomy catheter with backloading manifold 10 influences the operation of an embodiment of the present disclosure. Suitably strong and well directed ablation flow can take place with a guidewire 141 extending the full length of the enhanced cross stream mechanical thrombectomy catheter with backloading manifold 10 and/or additionally extending in a distal direction beyond the flexible tapered tip 26 and along the vasculature. Such ablation flow can be further improved, enhanced, modified or otherwise influenced by varying the location of or by full removal of the guidewire 141. With reference to FIG. 10, the guidewire 141, as shown, allows suitable transition for the high velocity fluid jets 136a-136n through the outflow orifice 22 to form cross stream jets 140a-140n which return via the inflow orifice 24. If, for example, the guidewire 141 is urged proximally to a guidewire end position 141a between the inflow orifice 24 and the outflow orifice 22, the inflow orifice 24 is totally unrestricted and has less flow resistance, thereby allowing greater and more forceful ingress of the cross stream jets 140a-140n laden with ablated thrombotic particulates 146, whereas the flow through the outflow orifice 22 remains substantially constant. Urging the guidewire 141 further in a proximal direction to a guidewire end position 141b distal to the outflow orifice 22 causes the outflow orifice 22 and the inflow orifice 24 both to be totally unrestricted and both to have less flow resistance, thereby allowing greater and more forceful flow from the outflow orifice 22, as well as resultantly increased ingress of the cross stream jets 140a-140n laden with ablated thrombotic particulates 146 through the inflow orifice 24. Each of the examples given above where the guidewire 141 is not totally removed from the smooth catheter tube 20 or other proximally located regions promotes sustained maceration of the loitering entrained ablated thrombotic particulates 146 where the smaller ablated thrombotic particulates 146 are exhausted proximally through the smooth catheter tube 20, the braided catheter tube 18, and the associated and pertinent structure proximal thereto. In another example, urging of the guidewire 141 to a position proximal of the proximal end of the braided catheter tube 18 or total removal of the guidewire 141, in addition to allowing total unrestricted flow through the outflow orifice 22 and the inflow orifice 24, allows unrestricted flow of ablated thrombotic particulates 146 along the smooth catheter tube 20, the braided catheter tube 18, and the associated and pertinent structure proximal thereto.

The preferred embodiment comprises a single outflow orifice 22, a corresponding cross stream jet which may be split in two by passage around high pressure tube 71, and a single inflow orifice 24.

Although the preferred embodiment as illustrated incorporates an inflow orifice 24 and an outflow orifice 22 aligned to the high pressure tube 71, one or both of the inflow or outflow orifices may be located so that they do not align with the high pressure tube; in this case, other means for guiding a guidewire past the orifice(s) is provided to prevent the guidewire from inadvertently passing through the non-aligned orifice(s).

The present disclosure also includes methods of treating a body vessel according to the aforementioned mode of operation.

Figure 12:
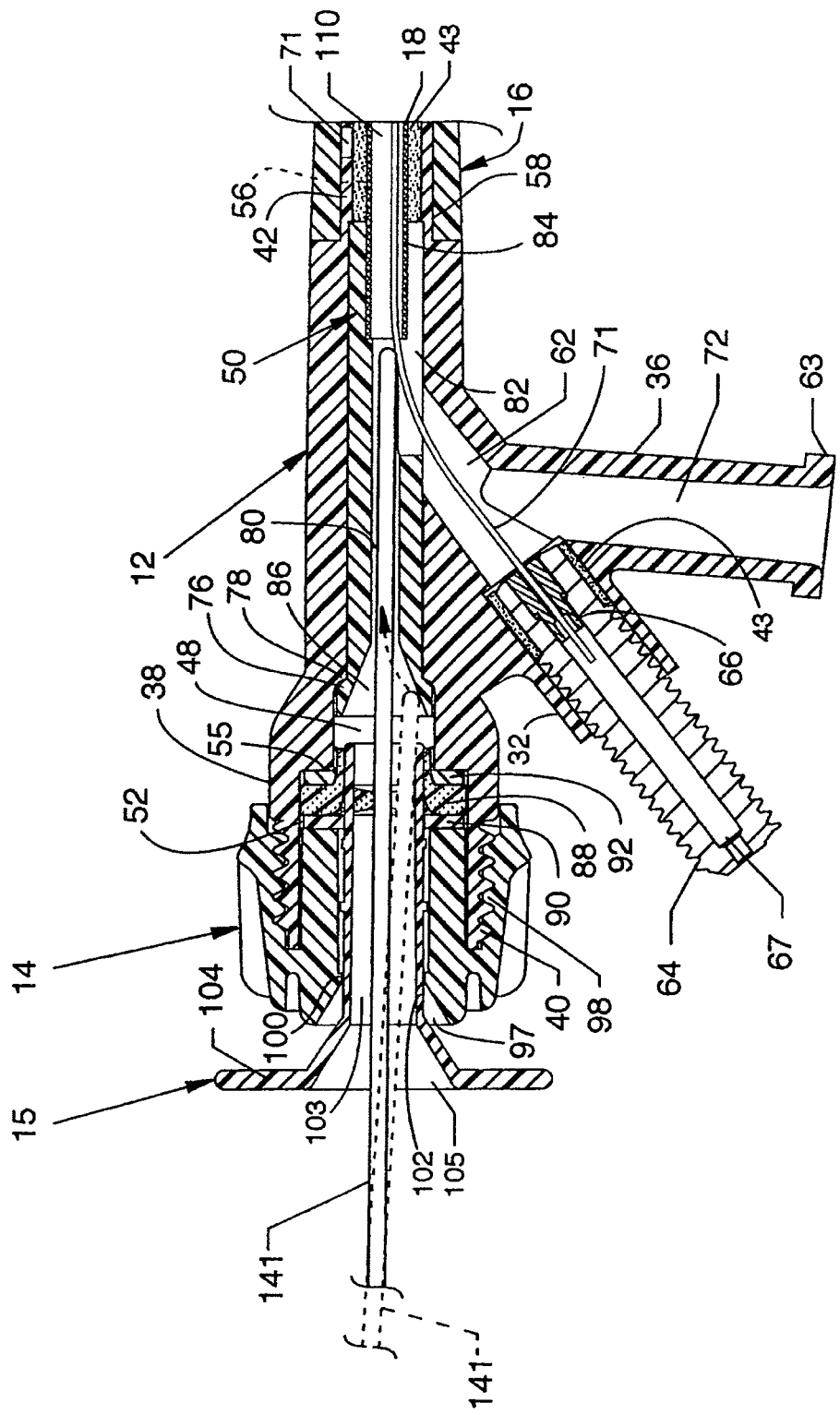
FIG. 12 is a side view in cross section illustrating the introduction of a guidewire into the enhanced cross stream mechanical thrombectomy catheter with backloading manifold.

FIG. 12 is a side view in cross section illustrating the introduction of the guidewire 141 into the enhanced cross stream mechanical thrombectomy catheter with backloading manifold 10. When it is desired to remove a guidewire, such as guidewire 141, or exchange guidewires having different attributes, backloading is facilitated by the structure of the insert 50. Loading can be accomplished, if necessary, using the introducer 15 to gain entry through the self-sealing hemostatic valve 88 where the introducer parts the sealing structure of the self-sealing hemostatic valve 88 to allow entry of the guidewire 141 therethrough. Otherwise the guidewire can pass unaided through the self-sealing hemostatic valve 88. The tip of the guidewire may not be in proper alignment with the central passageway 80, such as is shown by the guidewire 141 shown in dashed lines. In such case, impingement of the tip of the distally urged guidewire 141 with the conically-shaped beveled surface entrance 86 of central passageway 80 directs the tip of the guidewire 141 to align with and to be engaged within the central passageway 80 of the insert 50 and to be in alignment, as shown, within the central passageway 80 so as to align with and be subsequently engaged within the proximal portion of the braided catheter tube 18 for passage therethrough. Distal urging of the guidewire 141 also positions the tip of the guidewire 141 for passage through the distal region of the smooth catheter tube 20 where the geometry helpfully accommodates such passage by and along the outflow orifice 22 and the inflow orifice 24 and through the fluid jet emanator 116, the support ring 124, and the flexible tapered tip 26. Preferably, the tip of the guidewire 141 is dome-shaped. Such a dome shape is easily guided by and accommodated by the proximally-facing rounded surface of the terminated loop 117 of the fluid jet emanator 116. Use of the introducer 15 can also be utilized if front loading of a guidewire is required for passage through the self-sealing hemostatic valve 88. Preferably, the guidewire 141 exhibits sufficient size, flexibility and other attributes to navigate the tortuous vascular paths, but exhibits sufficient rigidity not to kink, bend or otherwise be permanently deformed and to stay within the appropriate confines of the distal portion of the smooth catheter tube 20 and not stray through the outflow orifice 22 or the inflow orifice 24. The cross sections of the outflow orifice 22 and the inflow orifice 24 are such that entry thereinto of the horizontally aligned guidewire of sufficient size and larger cross section profile is next to impossible. Notwithstanding, the use of one pair of inflow and outflow orifices further reduces the chance of inadvertent exiting of the guidewire tip through an orifice.

The present disclosure also includes methods of fabricating an enhanced cross stream mechanical thrombectomy catheter with backloading manifold including steps of providing components as disclosed herein and steps of aligning the provided components and steps of affixing the aligned provided components to retain the components in the aligned configuration as indicated in FIGS. 5, 7 and 10.

Figure 13:
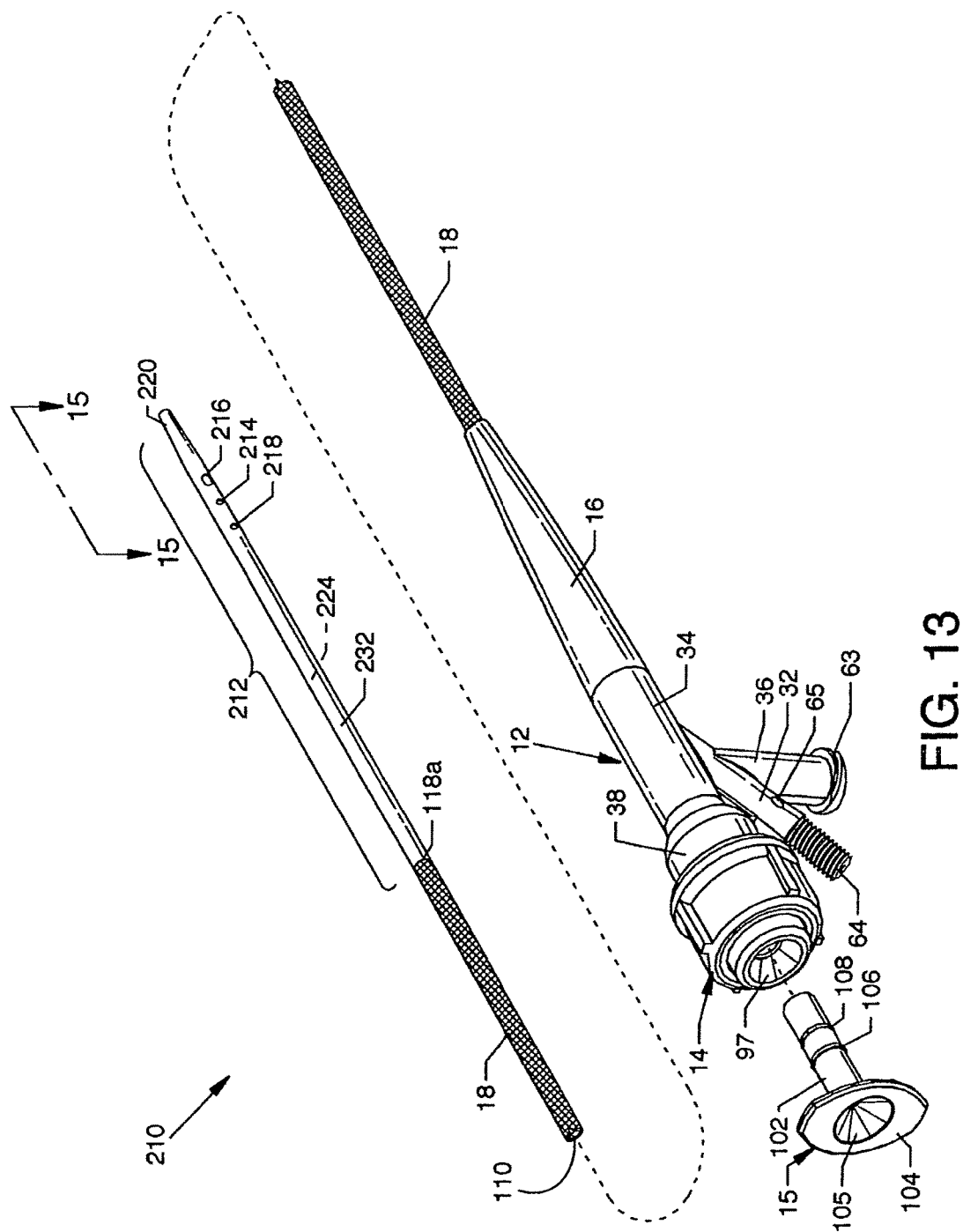
FIG. 13, a first alternative embodiment, is an isometric view of an enhanced cross stream mechanical thrombectomy catheter with backloading manifold.
Figure 15:
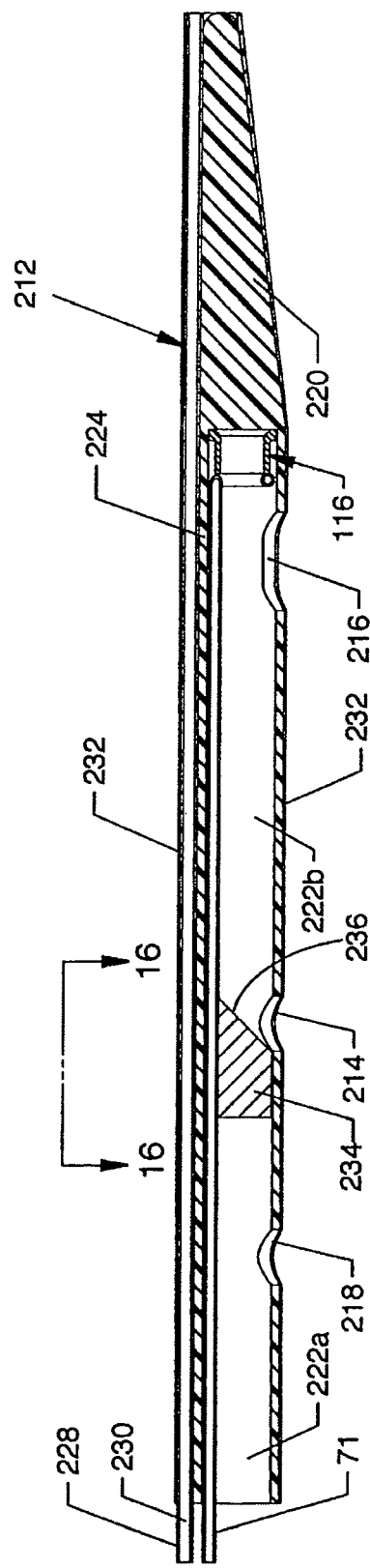
FIG. 15 is a cross section side view of the components of the distal region of the smooth catheter tube assembly along line 15-15 of FIG. 13.
Figure 18:
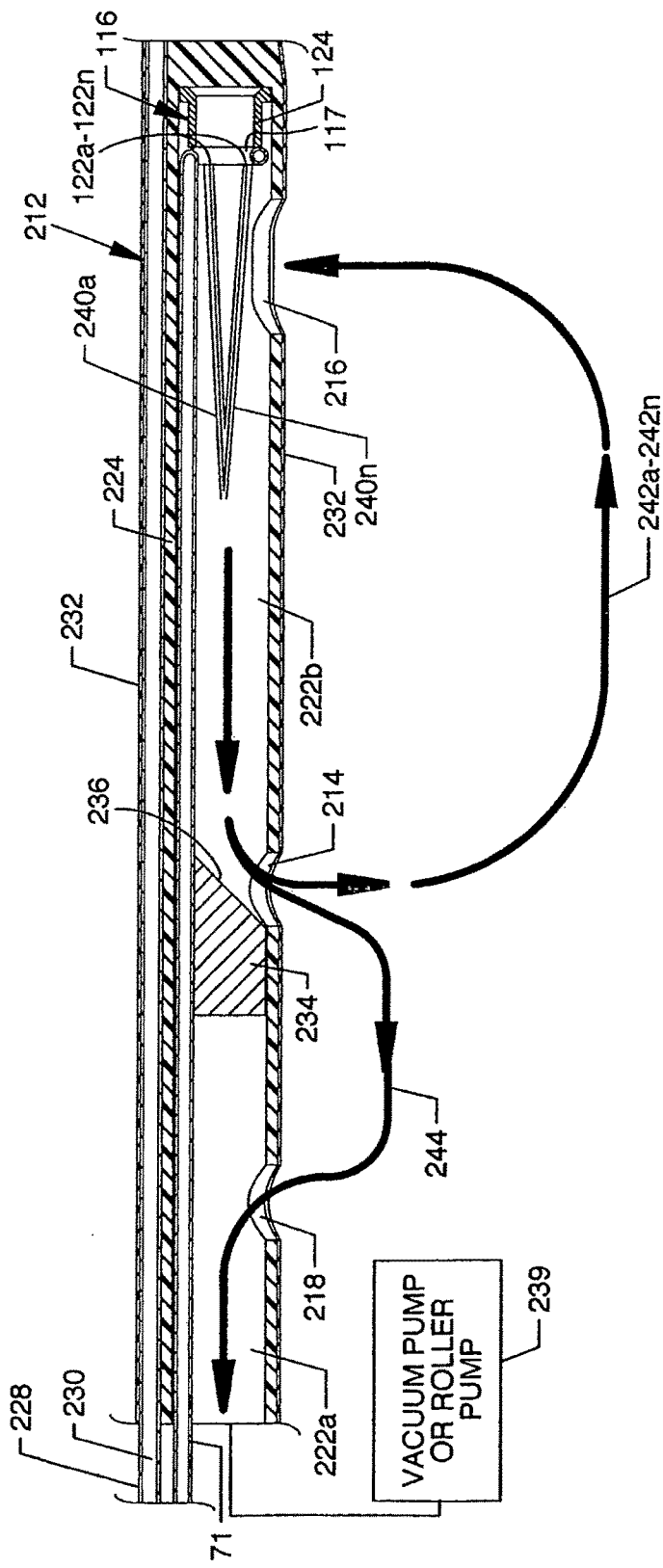
FIG. 18 illustrates the distal portion of the smooth catheter tube assembly of the first alternative embodiment in cross section.

FIG. 13, a first alternative embodiment, is an isometric view of an enhanced cross stream mechanical thrombectomy catheter with backloading manifold 210, incorporating much of the structure previously described, but differing in the substitution of a smooth catheter tube assembly 212 and other components and structure housed in the smooth catheter tube assembly 212 for the smooth catheter tube assembly 19 and previously described components and structure housed in the smooth catheter tube assembly 19. Also, previously described components are utilized including the components of or components attached to or associated with the centrally located backloading manifold 12 involving the hemostatic nut 14, the introducer 15, the flexible and tapered strain relief 16, and the braided catheter tube 18. The smooth catheter tube assembly 212 of multiple layer plastic composition is connected to and extends distally from the braided catheter tube 18 at a junction 118a and includes an outflow orifice 214, an inflow orifice 216, and additionally an evacuation orifice 218, each located in longitudinal alignment along an imaginary line at the distal portion of the smooth catheter tube assembly 212 near a flexible tapered tip 220 located distally at the end of the smooth catheter tube assembly 212 and each extending through the wall of the smooth catheter tube 224. For illustration purposes, the outflow orifice 214, the inflow orifice 216, and the evacuation orifice 218 are shown on the side of the smooth catheter tube assembly 212, but they can be located along any imaginary line extending longitudinally along a distal surface of the smooth catheter tube assembly 212, such as is shown in FIGS. 15 and 18.

Figure 14:
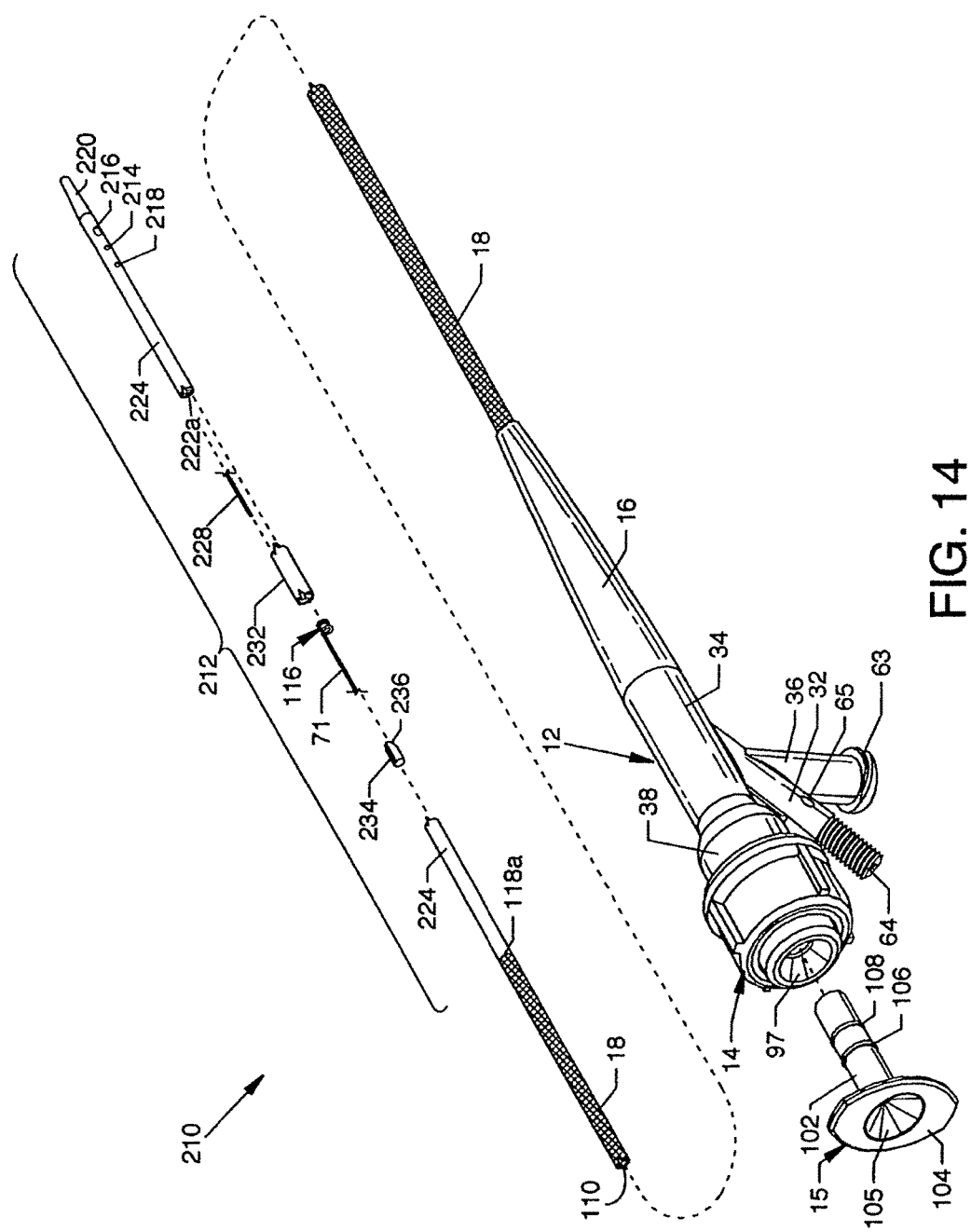
FIG. 14 is a partially exploded isometric view of the enhanced cross stream mechanical thrombectomy catheter with backloading manifold illustrated in FIG. 13.
Figure 16:
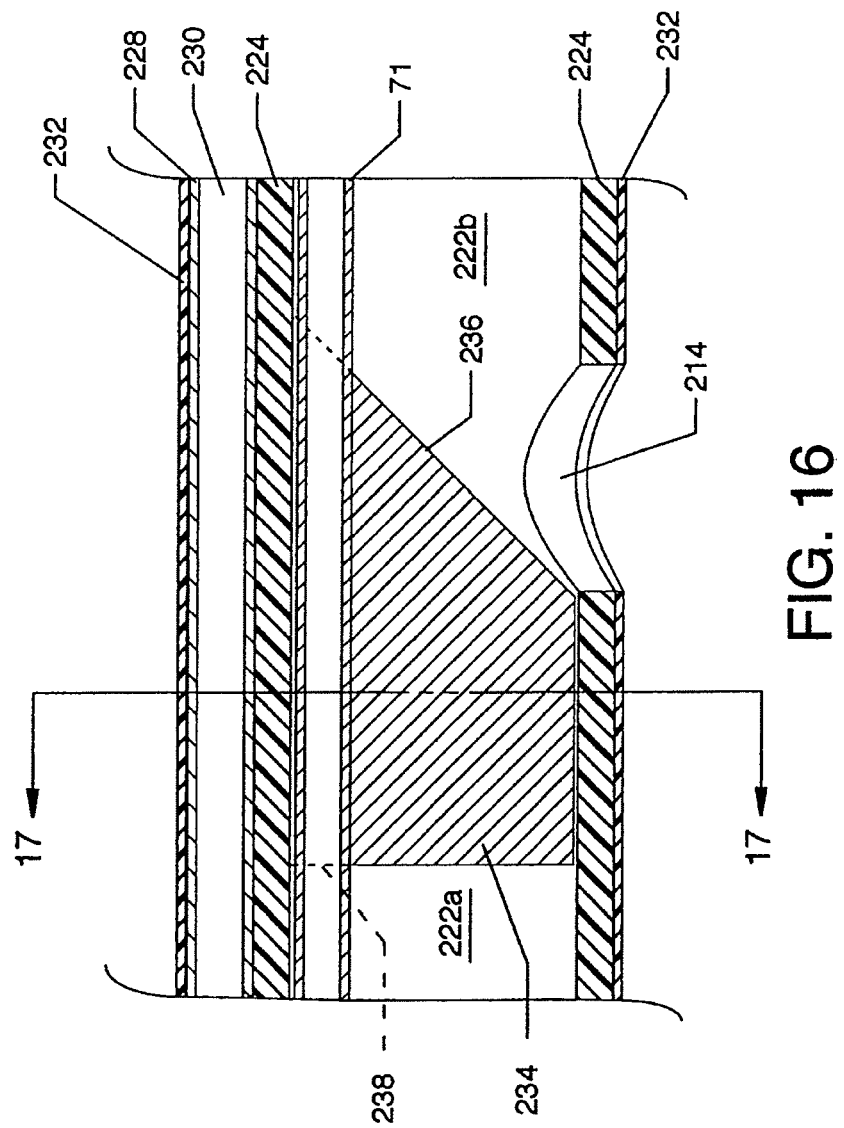
FIG. 16 is a magnified cross section view along line 16-16 of FIG. 15.

FIG. 14 is a partially exploded isometric view of the enhanced cross stream mechanical thrombectomy catheter with backloading manifold 210; FIG. 15 is a cross section side view of the components of the distal region of the smooth catheter tube assembly 212 along line 15-15 of FIG. 13; and FIG. 16 is a magnified cross section view along line 16-16 of FIG. 15. With reference to FIGS. 14, 15 and 16, the first alternative embodiment is now further described.

The smooth catheter tube assembly 212, the components of which are depicted fully in FIGS. 13 and 14, includes a centrally located smooth catheter tube 224, having lumens 222a and 222b, about which or in which other components are located, including a guidewire tube 228 having a lumen 230 which aligns preferably in opposition to the outflow orifice 214, the inflow orifice 216, and the evacuation orifice 218 along the opposing outer surface of the smooth catheter tube 224 and which extends along the smooth catheter tube 224 from and including the flexible tapered tip 220 to enter and pass within the lumen 110 of the braided catheter tube 18 at or near the junction 118a to the interior of the backloading manifold 12. A flexible plastic sheath 232, part of the smooth catheter tube assembly 212, encompasses the smooth catheter tube 224 and extends the length thereof from the flexible tapered tip 220 until reaching the junction 118a. The proximal portion of the high pressure tube 71 extends distally and through the lumen 110 of the braided catheter tube 18, and thence along the lumen 222a of and along the smooth catheter tube 224 to terminate as part of the fluid jet emanator 116 shown in FIG. 15 adjacent to the flexible tapered tip 220 at the distal end of the lumen 222b of the smooth catheter tube assembly 212. A deflector 234 in the form of a truncated solid structure and including a deflector face 236 suitably angled with respect to the longitudinal axis of the smooth catheter tube 224 is located between the lumens 222a and 222b of the smooth catheter tube 224 and defines the separation of the lumens 222a and 222b where lumen 222a extends proximally along the interior of the smooth catheter tube 224 from the deflector 234 in communication with the evacuation orifice 218 and where the lumen 222b extends distally from the deflector 234 in communication with the outflow orifice 214 and the inflow orifice 216 until terminating at the flexible tapered tip 220. The deflector 234 is located in close proximity to the outflow orifice 214 and is oriented to cause the deflection of the highly pressurized fluid jets projected proximally from the fluid jet emanator 116 to be reflectingly and deflectingly directed through the outflow orifice 214, as described later in detail. The deflector 234 aids in structural integrity of the distal portion of the smooth catheter tube 224 as does the structure of the fluid jet emanator 116. Also shown in FIG. 14 is the junction 118a between the smooth catheter tube assembly 212 and the braided catheter tube 18, such junction being suitably effected to provide for a smooth and continuous coupling of the smooth catheter tube assembly 212 and the braided catheter tube 18.

Figure 17:
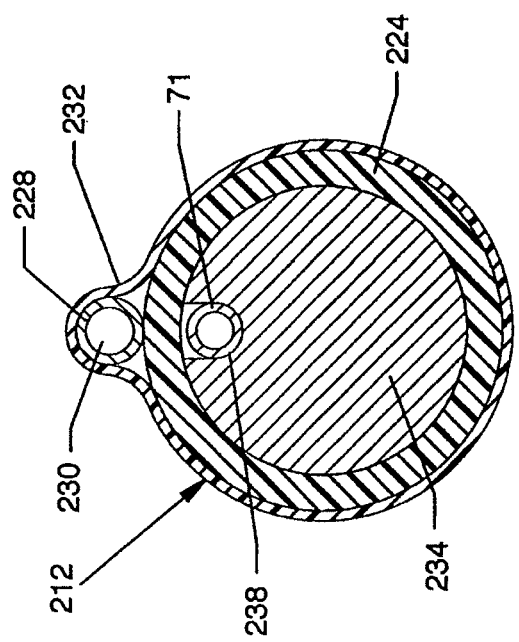
FIG. 17 is a cross section view of the smooth catheter tube assembly along line 17-17 of FIG. 16.

FIG. 17 is a cross section view of the smooth catheter tube assembly 212 along line 17-17 of FIG. 16. Shown in particular is an elongated slot 238 extending longitudinally through the upper surface of the deflector 234 through which the high pressure tube 71 passes and secures such as by welding or other suitable means. Also shown is the sheath 232 surroundingly encompassing the smooth catheter tube 224 and the guidewire tube 228, thereby securing the guidewire tube 228 to the smooth catheter tube 224.

Mode of Operation

The mode of operation of the enhanced cross stream mechanical thrombectomy catheter with backloading manifold 210 is explained with reference to FIGS. 18 and 19. FIG. 18 illustrates the distal portion of the smooth catheter tube assembly 212 in cross section and the use of a vacuum source, such as a vacuum pump or roller pump 239, which connects through the lumen 222a of the smooth catheter tube 224 to the exhaust branch 36 of the backloading manifold 12. High velocity fluid jets 240a-240n are shown emanating proximally from the plurality of jet orifices 122a-122n of the terminated loop 117 of the fluid jet emanator 116 into the lumen 222b of the smooth catheter tube 224 for subsequent creation of and culminating in cross stream jets 242a-242n, shown by heavy lines, where the high velocity fluid jets 240a-240n are concentratingly deflected and redirected by the deflector face 236 of the deflector 234 to flow as cross stream jets 242a-242n from the outflow orifice 214 and return through the inflow orifice 216 while accomplishing ablative action with adhered blood vessel thrombus foreign material and for maceration of foreign material in concert with the high velocity fluid jets 240a-240n. A great preponderance of foreign material is introduced through the inflow orifice 216 and into the lumen 222b after dislodging from a blood vessel wall for macerating impingement by the high velocity fluid jets 240a-240n. Macerated small mass foreign material, i.e., thrombotic particulate, contained in the cross stream jets 242a-242n, especially that foreign material near the outflow orifice 214, is drawn from the flow of the cross stream jets 242a-242n by the relatively low pressure area presented at the evacuation orifice 218 along an additional and proximally directed flow 244 from the outflow orifice 214 to the evacuation orifice 218 and thence proximally through and within the lumen 222a of the smooth catheter tube 224, as also depicted by heavy lines. A previously placed guidewire (not shown) is incorporated to load the enhanced cross stream mechanical thrombectomy catheter with backloading manifold 210 within the vasculature by first utilizing the distal end of the lumen 230 of the guidewire tube 228 followed by subsequent advancement by the enhanced cross stream mechanical thrombectomy catheter with backloading manifold 210 along the guidewire in close proximity to a thrombus site. In the alternative, the first guidewire can be withdrawn completely from the enhanced cross stream mechanical thrombectomy catheter with backloading manifold 210 and swapped by backloading with another guidewire of other properties and attributes if required. An advantage of an embodiment of the present disclosure is that the guidewire can be introduced by a front loading approach or by a backloading approach and, therefore, the guidewire can be removed and reintroduced or can be replaced by a different guidewire.

Figure 19:
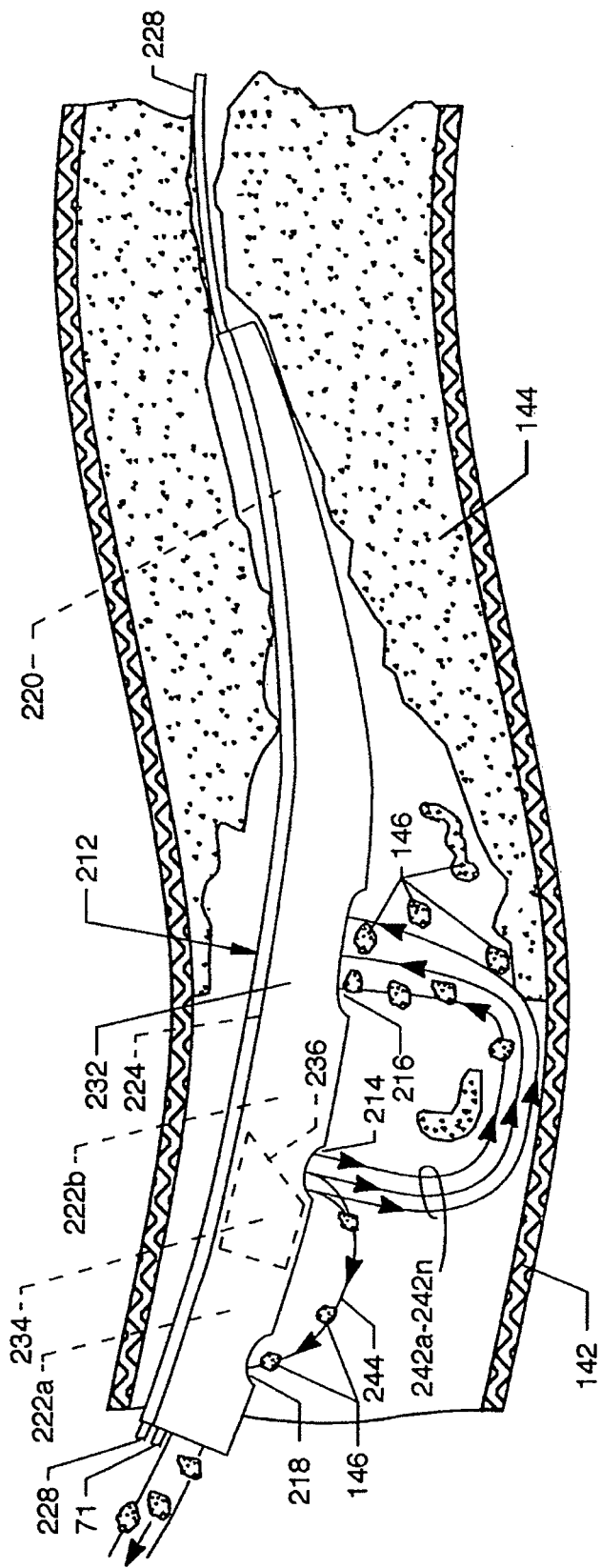
FIG. 19 is a side view of the distal region of the enhanced cross stream mechanical thrombectomy catheter with backloading manifold constituting the first alternative embodiment showing the distal end of the smooth catheter tube assembly positioned in a blood vessel (shown in cross section) at a site of a thrombotic deposit or lesion.

FIG. 19 is a side view of the distal region of the enhanced cross stream mechanical thrombectomy catheter with backloading manifold 210 showing in particular the distal end of the smooth catheter tube assembly 212 positioned in a blood vessel 142 (shown in cross section) at a site of a thrombotic deposit or lesion 144. While FIG. 19 depicts the smooth catheter tube assembly 212 as being in a blood vessel in particular, it is to be understood that it is not limited to use in a blood vessel, but has utility with respect to any body cavity in general. High velocity fluid jets 240a-240n (shown in FIG. 18) of saline or other suitable solution are emanated or emitted in a proximal direction from the fluid jet emanator 116 into the smooth catheter tube 224 and pass through the outflow orifice 214 creating cross stream jets 242a-242n directed toward the wall of the blood vessel 142 having thrombotic deposits or lesions 144 and thence are influenced by the low pressure at the inflow orifice 216 to cause the cross stream jets 242a-242n to be directed distally substantially parallel to the central axis of the blood vessel 142 to impinge and break up thrombotic deposits or lesions 144 and to, by entrainment, urge and carry along the dislodged and ablated thrombotic particulate 146 of the thrombotic deposits or lesions 144 through the inflow orifice 216, a relatively low pressure region, and into the lumen 222b, which functions as a recycling maceration lumen or chamber or some thrombotic particulate 146 may enter the evacuation orifice 218. The entrainment through the inflow orifice 216 is facilitated by a low pressure source presented by the high velocity fluid jets 240a-240n. The outflow is driven in part by internal pressure which is created by the high velocity fluid jets 240a-240n, but more generally, outflow drive is caused by the suction (low pressure region) at the evacuation orifice 218 and proximally along lumen 222a as provided by the vacuum pump or roller pump 239. The enhanced clot removal is enabled by of the recirculation pattern established between inflow and outflow orifices 216 and 214, which creates a flow field that maximizes drag force on wall-adhered thrombus, and because of impingement of the cross stream jets 242a-242n. The cross stream jets 242a-242n, while being forcefully directed outwardly and toward the wall of the blood vessel 142 by opposite reaction, urge the distal portion of the smooth catheter tube 224 in the direction opposite the outward flow direction and away from the impingement area of the cross stream jets 242a-242n with the immediate thrombotic deposit or lesion 144 and/or the wall of the blood vessel 142, thus distancing the highly concentrated cross stream jets 242a-242n from the immediate thrombotic deposit or lesion 144 and/or the wall of the blood vessel 142, and thereby minimizing potential blood vessel-wall damage. Such distancing also removes the inflow orifice 216 from close proximity with and away from the opposed wall of the blood vessel 142, thereby minimizing the chance of ingestion of the blood vessel 142 wall structure by the inflow orifice 216.

The cross stream jets 242a-242n traversing between the outflow orifice 214 and the inflow orifice 216 combine to offer an enhanced broad cross section ablation area, such area having a breadth substantially larger and having more concentrated force than prior art devices using multiple inflow and outflow orifices where cross streams are of diminished force and breadth. Having a concentrated flow combining cross stream jets 242a-242n offers selective and directed ablation to take place. Prior art devices using multiple inflow and outflow orifices and having multiple flow areas generate cross streams which are equally weak in all directions, as the flow force is divided between the multiple flow streams, whereby ablation forces cannot be concentrated where desired. The distal end of the smooth catheter tube 224 can be rotated axially to direct the cross stream jets 242a-242n about a longitudinal axis to have 360.degree. coverage or can be rotated axially to offer coverage partially about the longitudinal axis or can be operated to and fro, as required.

Figure 20:
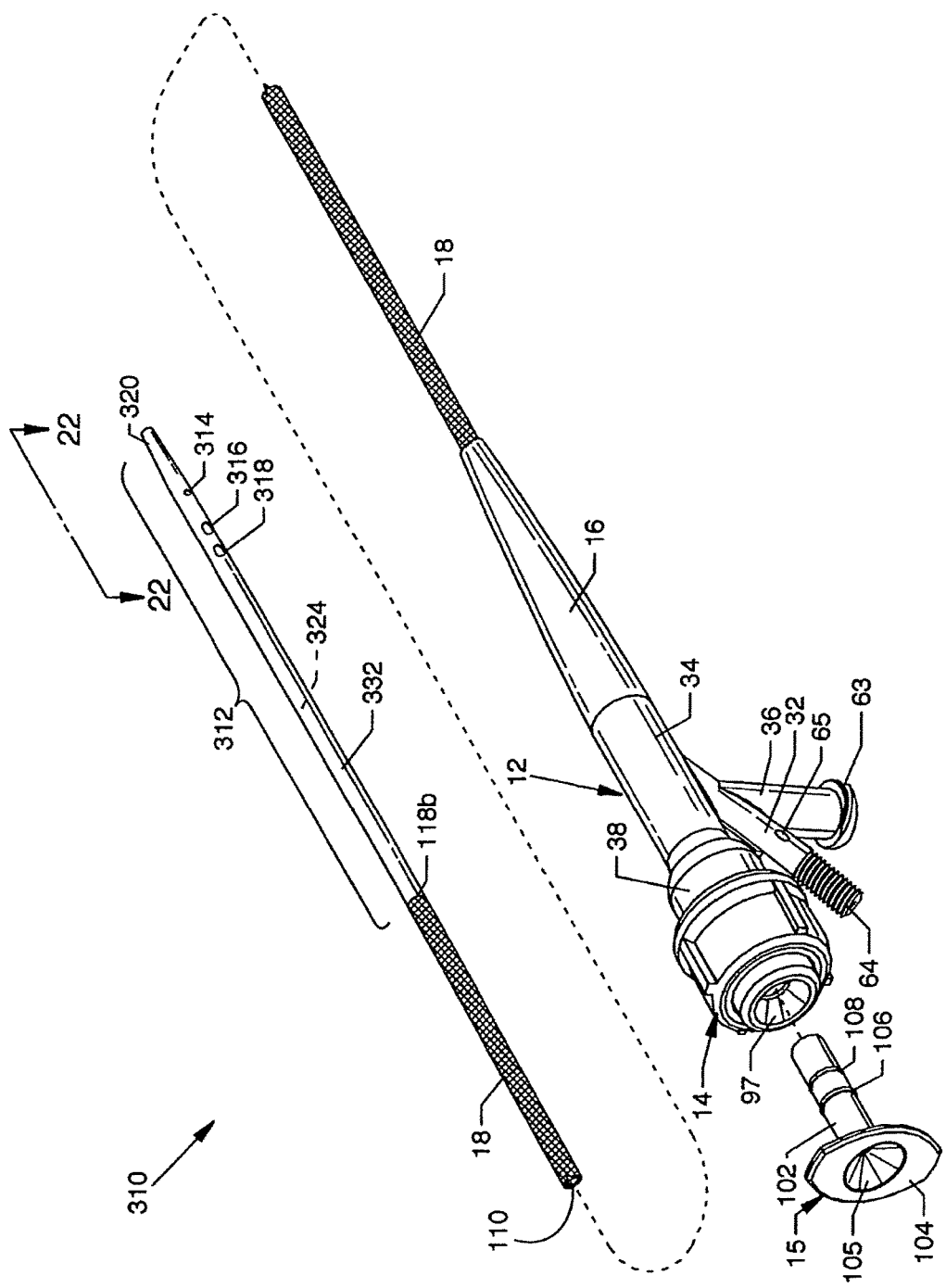
FIG. 20, a second alternative embodiment, is an isometric view of an enhanced cross stream mechanical thrombectomy catheter with backloading manifold.
Figure 22:
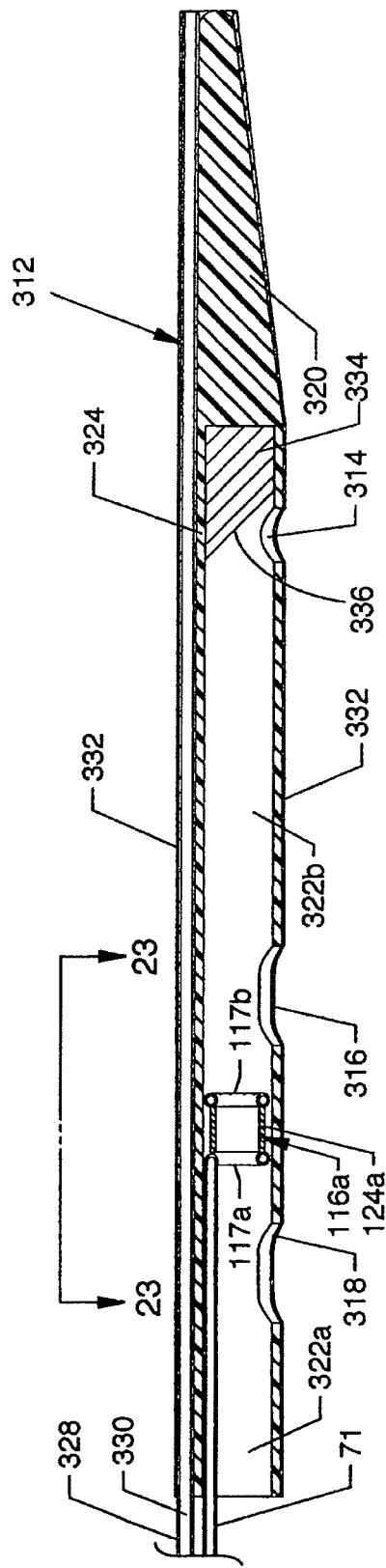
FIG. 22 is a cross section side view of the components of the distal region of the smooth catheter tube assembly along line 22-22 of FIG. 20.
Figure 25:
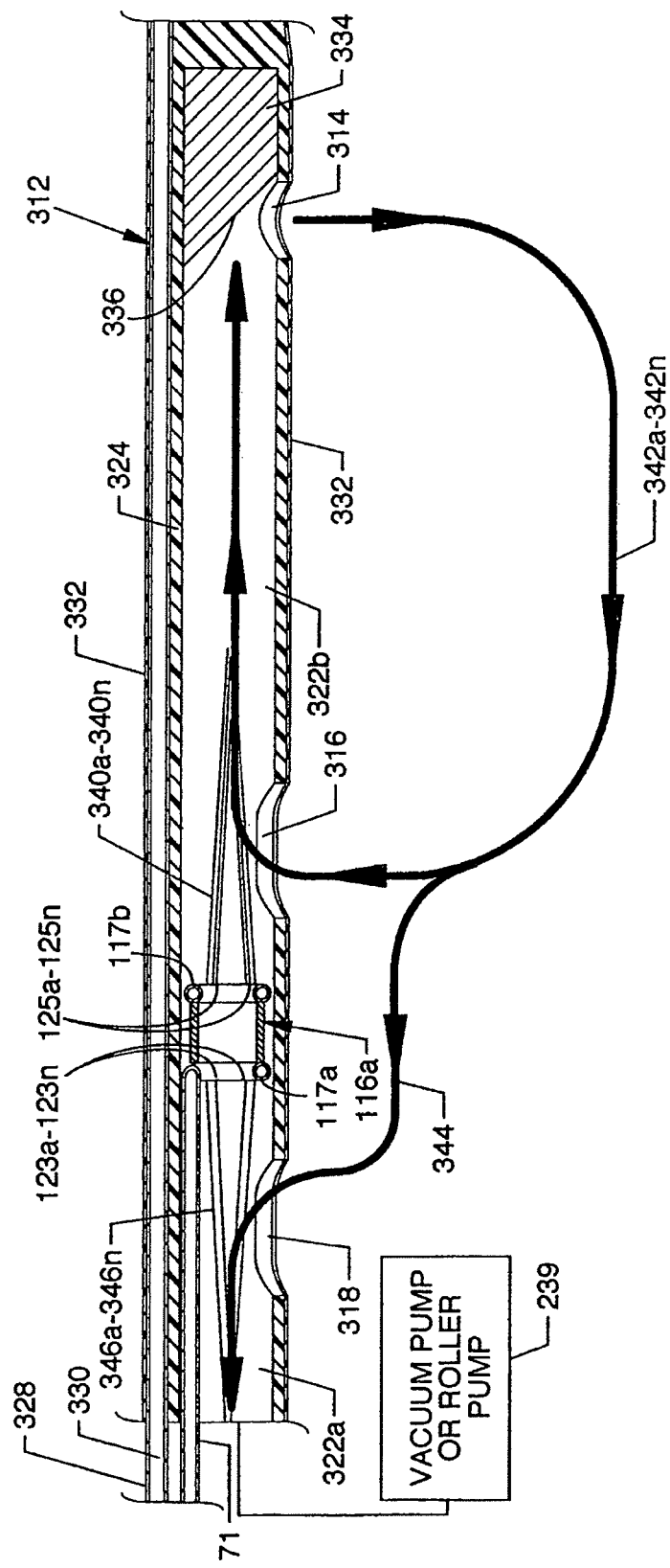
FIG. 25 illustrates the distal portion of the smooth catheter tube assembly of the second alternative embodiment in cross section.

FIG. 20, a second alternative embodiment, is an isometric view of an enhanced cross stream mechanical thrombectomy catheter with backloading manifold 310 incorporating much of the structure previously described, especially that of the first alternative embodiment, but differing from the preferred embodiment, as does the first alternative embodiment, by the substitution of, for example, a smooth catheter tube assembly 312 and other components and structure housed in the smooth catheter tube assembly 312 for the smooth catheter tube assembly 212, and previously described components and structure housed in the smooth catheter tube assembly 212. Also, previously described components are utilized including the components of or components attached to or associated with the centrally located backloading manifold 12 involving the hemostatic nut 14, the introducer 15, the flexible and tapered strain relief 16, and the braided catheter tube 18. In the second alternative embodiment, the smooth catheter tube assembly 312 of multiple layer plastic composition is connected to and extends distally from the braided catheter tube 18 at a junction 118b and includes an outflow orifice 314, an inflow orifice 316, and an evacuation orifice 318, each located in longitudinal alignment along an imaginary line at the distal portion of the smooth catheter tube assembly 312 near a flexible tapered tip 320 located distally at the end of the smooth catheter tube assembly 312. For illustration purposes, the outflow orifice 314, the inflow orifice 316, and the evacuation orifice 318 which extend through the wall of the smooth catheter tube 324 are shown on the side of the smooth catheter tube assembly 312, but they can be located along any imaginary line extending longitudinally along a distal surface of the smooth catheter tube assembly 312, such as is shown in FIGS. 22 and 25.

Figure 21:
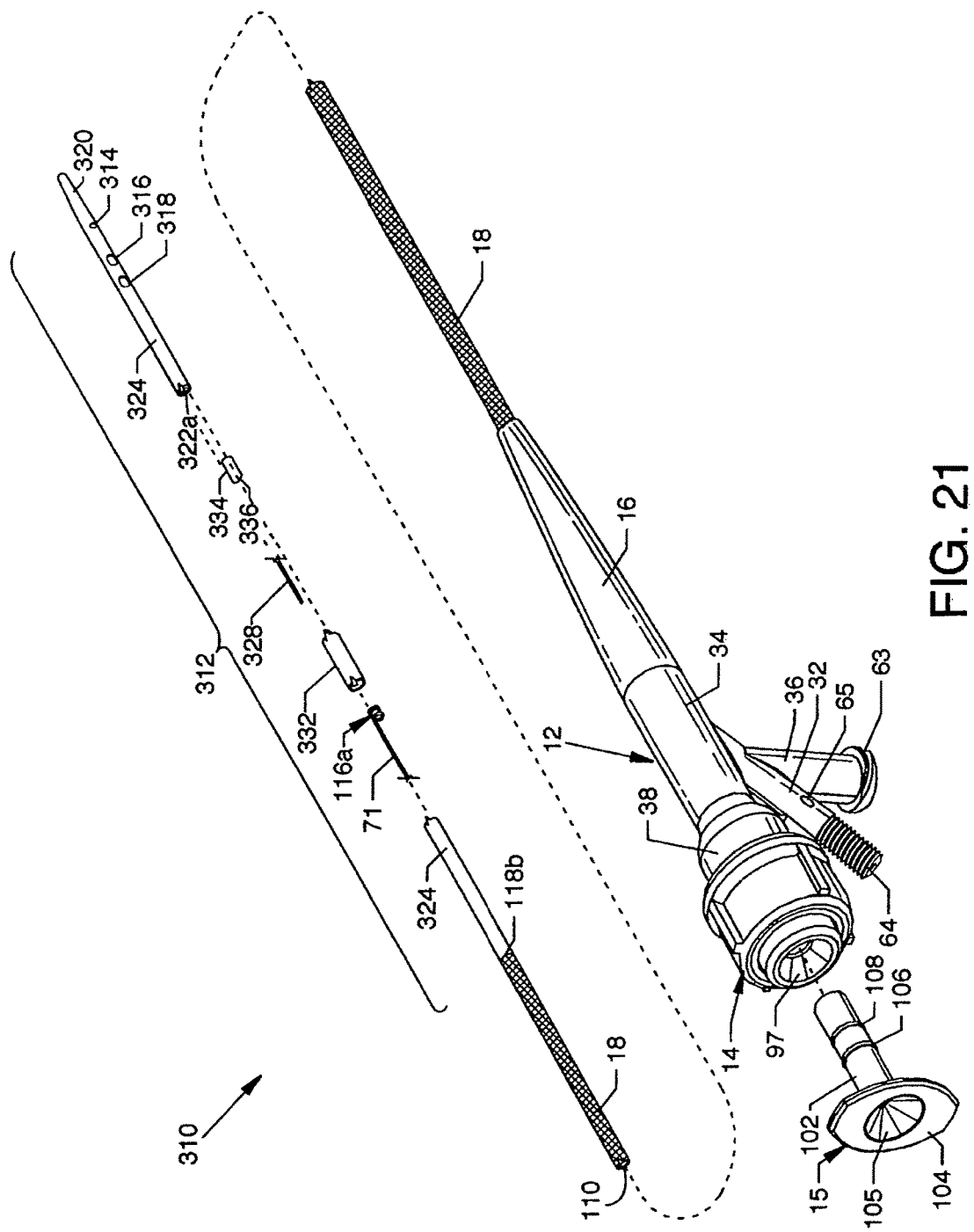
FIG. 21 is a partially exploded isometric view of the enhanced cross stream mechanical thrombectomy catheter with backloading manifold illustrated in FIG. 20.
Figure 23:
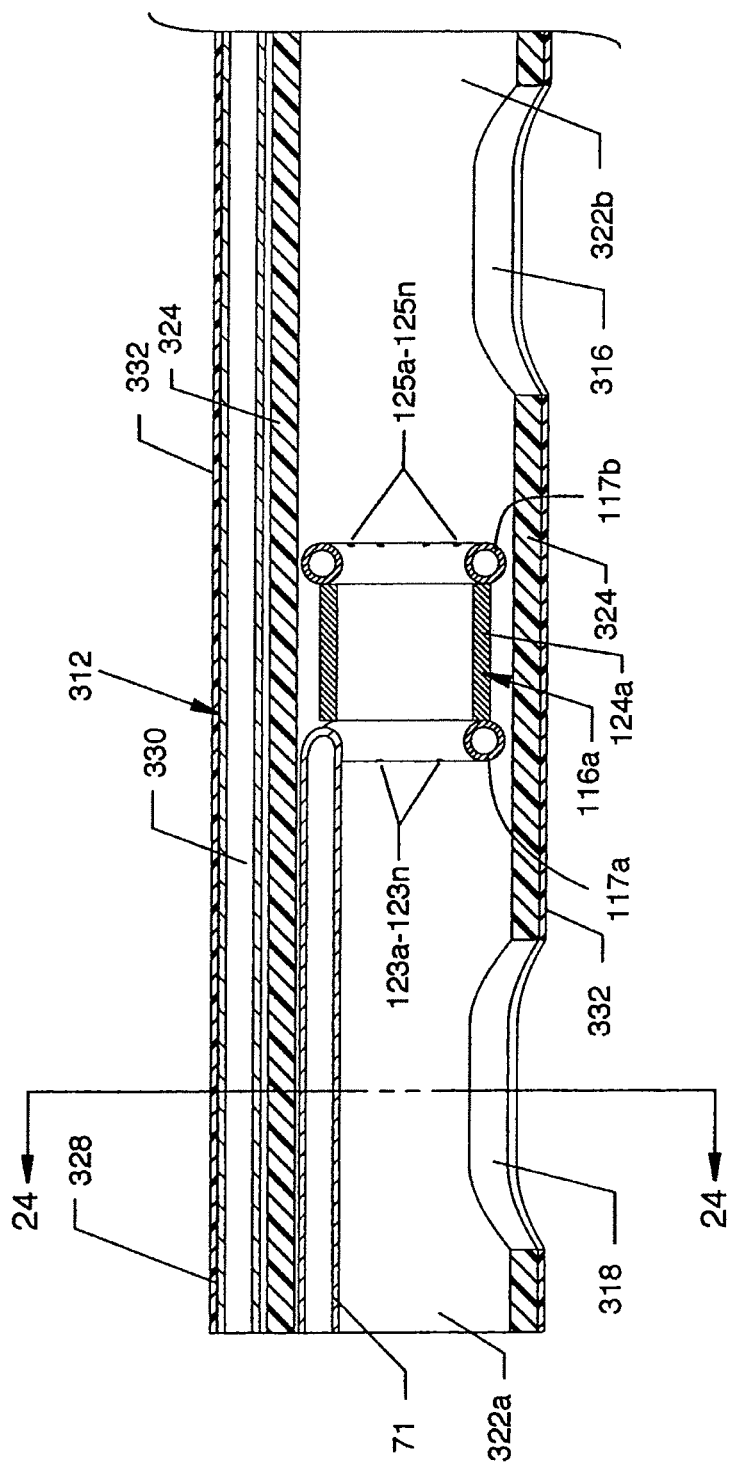
FIG. 23 is a magnified cross section view along line 23-23 of FIG. 22.

FIG. 21 is a partially exploded isometric view of the enhanced cross stream mechanical thrombectomy catheter with backloading manifold 310; FIG. 22 is a cross section side view of the components of the distal region of the smooth catheter tube assembly 312 along line 22-22 of FIG. 20; and FIG. 23 is a magnified cross section view along line 23-23 of FIG. 22. With reference to FIGS. 21, 22 and 23, the second alternate embodiment is now further described.

The smooth catheter tube assembly 312, the components of which are depicted fully in FIGS. 20 and 21, includes a centrally located smooth catheter tube 324 having lumens 322a and 322b, about which or in which other components are located, including a guidewire tube 328 having a lumen 330 which aligns preferably in opposition to the outflow orifice 314, the inflow orifice 316, and the evacuation orifice 318 along the opposing outer surface of the smooth catheter tube 324 and which extends along the smooth catheter tube 324 from and including the flexible tapered tip 320 to enter and pass within the lumen 110 of the braided catheter tube 18 at or near the junction 118b to the interior of the backloading manifold 12. A flexible plastic sheath 332, part of the smooth catheter tube assembly 312, encompasses the smooth catheter tube 324 and extends the length thereof from the flexible tapered tip 320 until reaching the junction 118b. The proximal portion of the high pressure tube 71 extends distally and through the lumen 110 of the braided catheter tube 18, and thence along the lumen 322a of and along the smooth catheter tube 324 to terminate as part of a multidirectional fluid jet emanator 116a shown in FIG. 22. In this embodiment, the multidirectional fluid jet emanator 116a is located between the inflow orifice 316 and the evacuation orifice 318 of the smooth catheter tube 324 and defines the separation of the lumens 322a and 322b where lumen 322a extends proximally along the interior of the smooth catheter tube 324 from the multidirectional fluid jet emanator 116a in communication with the evacuation orifice 318 and where the lumen 322b extends distally from the multidirectional fluid jet emanator 116a in communication with the inflow orifice 316 and the outflow orifice 314 until terminating at a deflector 334 adjacent to the flexible tapered tip 320. The deflector 334, in the form of a truncated solid structure and including a deflector face 336 suitably angled with respect to the longitudinal axis of the smooth catheter tube 324, is located at the distal end of the lumen 322b in close proximity and slightly distal of the outflow orifice 314 and is oriented to cause the deflection of the high velocity fluid jets projected distally from the multidirectional fluid jet emanator 116a to be reflectingly and deflectingly directed through the outflow orifice 314, as described later in detail. The deflector 334 aids in structural integrity of the distal portion of the smooth catheter tube 324 as does the structure of the multidirectional fluid jet emanator 116a. Also shown in FIG. 21 is the junction 118b between the smooth catheter tube assembly 312 and the braided catheter tube 18, such junction being suitably effected to provide for a smooth and continuous coupling of the smooth catheter tube assembly 312 and the braided catheter tube 18. FIG. 23 best illustrates the multidirectional fluid jet emanator 116a which is a variation of the previously described fluid jet emanator 116. The multidirectional fluid jet emanator 116a includes features found in the fluid jet emanator 116, but the terminated loop 117 of the fluid jet emanator 116 is replaced by a proximal loop 117a, and a connected distal loop 117b is added. Both the proximal loop 117a and the distal loop 117b are in communication with each other and with the high pressure tube 71 and they are located on opposing ends of a support ring 124a. A plurality of proximally directed jet orifices 123a-123n are located on the proximal side of the proximal loop 117a, and a plurality of distally directed jet orifices 125a-125n are located on the distal side of the distal loop 117b for simultaneous emanation of high velocity fluid jets in opposite directions. The multidirectional fluid jet emanator 116a is suitably affixed within the smooth catheter tube 324 between the inflow orifice 316 and the evacuation orifice 318.

Figure 24:
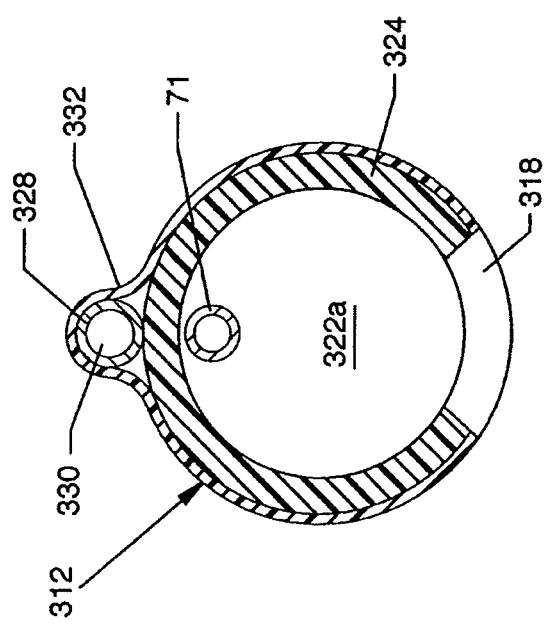
FIG. 24 is a cross section view of the smooth catheter tube assembly along line 24-24 of FIG. 23.

FIG. 24 is a cross section view of the smooth catheter tube assembly 312 along line 24-24 of FIG. 23. Shown in particular is the evacuation orifice 318 which passes through both the plastic sheath 332 and the smooth catheter tube 324.

Mode of Operation

The mode of operation of the enhanced cross stream mechanical thrombectomy catheter with backloading manifold 310 is explained with reference to FIGS. 25 and 26. FIG. 25 illustrates the distal portion of the smooth catheter tube assembly 312 in cross section and the use of an optional vacuum source, such as a vacuum pump or roller pump 339, which connects through the lumen 322a of the smooth catheter tube 324 to the exhaust branch 36 of the backloading manifold 12. High velocity fluid jets 340a-340n are shown emanating distally from the plurality of jet orifices 125a-125n in the distal loop 117b of the fluid jet emanator 116 into the lumen 322b of the smooth catheter tube 324 for subsequent creation of and culminating in cross stream jets 342a-342n, as shown by heavy lines, where the high velocity fluid jets 340a-340n are concentratingly deflected and redirected by the deflector face 336 of the deflector 334 to flow as cross stream jets 342a-342n from the outflow orifice 314 and return through the inflow orifice 316 while accomplishing ablative action with adhered blood vessel thrombus foreign material and for maceration of foreign material in concert with the high velocity fluid jets 340a-340n. A great preponderance of foreign material is introduced through the inflow orifice 316 and into the lumen 322b after dislodging from a blood vessel wall for macerating impingement by the high velocity fluid jets 340a-340n. Macerated small mass foreign material, i.e., thrombotic particulate, contained in the cross stream jets 342a-342n, especially that foreign material near the inflow orifice 316, is drawn from the flow of the cross stream jets 342a-342n by the relatively low pressure area presented at the evacuation orifice 318 along an additional and proximally directed flow 344 from near the inflow orifice 316 to the evacuation orifice 318 and thence proximally through and within the lumen 322a of the smooth catheter tube 324, as also depicted by heavy lines. Proximally directed high velocity fluid jets 346a-346n emanating proximally from the plurality of jet orifices 123a-123n in the proximal loop 117a into the lumen 322a of the smooth catheter tube 324 create the relatively low pressure presented at the evacuation orifice 318 to draw thrombotic particulate through the evacuation orifice 318 and to provide a proximally directed driving force to urge the thrombotic particulate proximally along the lumen 322a.

A previously placed guidewire (not shown) is incorporated to load the enhanced cross stream mechanical thrombectomy catheter with backloading manifold 310 within the vasculature by first utilizing the distal end of the lumen 330 of the guidewire tube 328 followed by subsequent advancement by the enhanced cross stream mechanical thrombectomy catheter with backloading manifold 310 along the guidewire in close proximity to a thrombus site. In the alternative, the first guidewire can be withdrawn completely from the enhanced cross stream mechanical thrombectomy catheter with backloading manifold 310 and swapped by backloading with another guidewire of other properties and attributes, if required. An advantage of an embodiment of the present disclosure is that the guidewire can be introduced by a front loading approach or by a backloading approach and, therefore, the guidewire can be removed and reintroduced or can be replaced by a different guidewire.

Figure 26:
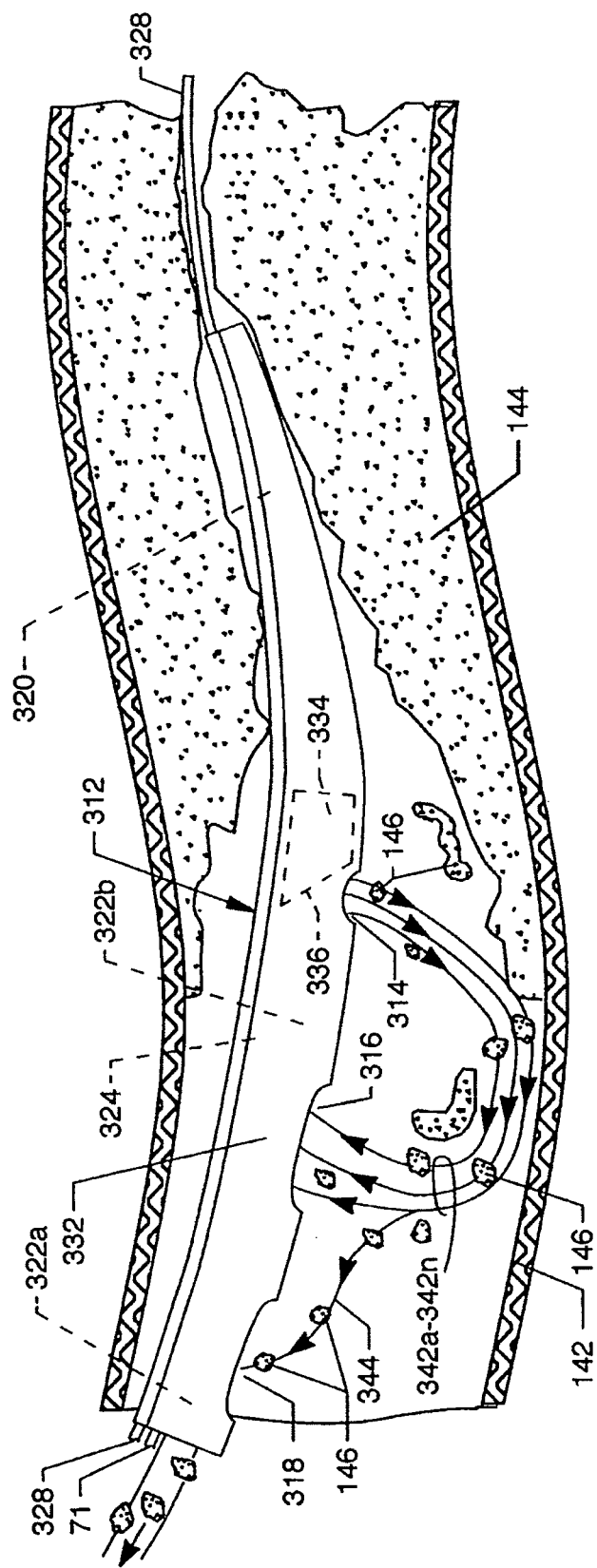
FIG. 26 is a side view of the distal region of the enhanced cross stream mechanical thrombectomy catheter with backloading manifold constituting the second alternative embodiment showing the distal end of the smooth catheter tube assembly positioned in a blood vessel (shown in cross section) at a site of a thrombotic deposit or lesion.

FIG. 26 is a side view of the distal region of the enhanced cross stream mechanical thrombectomy catheter with backloading manifold 310 showing in particular the distal end of the smooth catheter tube assembly 312 positioned in a blood vessel 142 (shown in cross section) at a site of a thrombotic deposit or lesion 144. While FIG. 26 depicts the smooth catheter tube assembly 312 as being in a blood vessel in particular, it is to be understood that it is not limited to use in a blood vessel but has utility with respect to any body cavity in general. High velocity fluid jets 340a-340n (shown in FIG. 25) of saline or other suitable solution are emanated or emitted in a distal direction from the multidirectional fluid jet emanator 116a into the lumen 322b of the smooth catheter tube 324 and are concentratingly deflected and redirected by the deflector 334 to pass through the outflow orifice 314 creating cross stream jets 342a-342n directed toward the wall of the blood vessel 142 having thrombotic deposits or lesions 144 and thence are influenced by the low pressure at the inflow orifice 316 to cause the cross stream jets 342a-342n to be directed proximally substantially parallel to the central axis of the blood vessel 142 to impinge and break up thrombotic deposits or lesions 144 and to, by entrainment, urge and carry along the dislodged and ablated thrombotic particulate 146 of the thrombotic deposits or lesions 144 through the inflow orifice 316, a relatively low pressure region, and into the lumen 322b, which functions as a recycling maceration lumen or chamber, or some thrombotic particulate 146 may enter the evacuation orifice 318. The entrainment through the evacuation orifice 318 is facilitated by a low pressure source presented by the high velocity fluid jets 346a-346n directed proximally along the lumen 322a for entrainment of thrombotic particulate 146 along the path of the proximally directed flow 344 for ingestion of thrombotic particulate 146 through the evacuation orifice 318. The outflow is driven by internal pressure which is created by the high velocity fluid jets 346a-346n proximally directed along the lumen 322a, but alternatively, the outflow drive can be assisted by the suction (low pressure region) at the lumen 322a as provided by the vacuum pump or roller pump 339. The enhanced clot removal is enabled by the recirculation pattern established between inflow and outflow orifices 316 and 314, which creates a flow field that maximizes drag force on wall-adhered thrombus, and because of impingement of the cross stream jets 342a-342n. The cross stream jets 342a-342n, while being forcefully directed outwardly and toward the wall of the blood vessel 142 by opposite reaction, urge the distal portion of the smooth catheter tube 324 in the direction opposite the outward flow direction and away from the impingement area of the cross stream jets 342a-342n with the immediate thrombotic deposit or lesion 144 and/or the wall of the blood vessel 142, thus distancing the highly concentrated cross stream jets 342a-342n from the immediate thrombotic deposit or lesion 144 and/or the wall of the blood vessel 142, and thereby minimizing potential blood vessel wall damage. Such distancing also removes the inflow orifice 316 from close proximity with and away from the opposed wall of the blood vessel 142, thereby minimizing the chance of ingestion of the blood vessel 142 wall structure by the inflow orifice 316.

The cross stream jets 342a-342n traversing between the outflow orifice 314 and the inflow orifice 316 combine to offer an enhanced broad cross section ablation area, such area having a breadth substantially larger and having more concentrated force than prior art devices using multiple inflow and outflow orifices where cross streams are of diminished force and breadth. Having a concentrated flow combining cross stream jets 342a-342n offers selective and directed ablation to take place. Prior art devices using multiple inflow and outflow orifices and having multiple flow areas generate cross streams which are equally weak in all directions, as the flow force is divided between the multiple flow streams, whereby ablation forces cannot be concentrated where desired. The distal end of the smooth catheter tube 324 can be rotated axially to direct the cross stream jets 342a-342n about a longitudinal axis to have 360.degree. coverage or can be rotated axially to offer coverage partially about the longitudinal axis or can be operated to and fro, as required.

Figure 27:
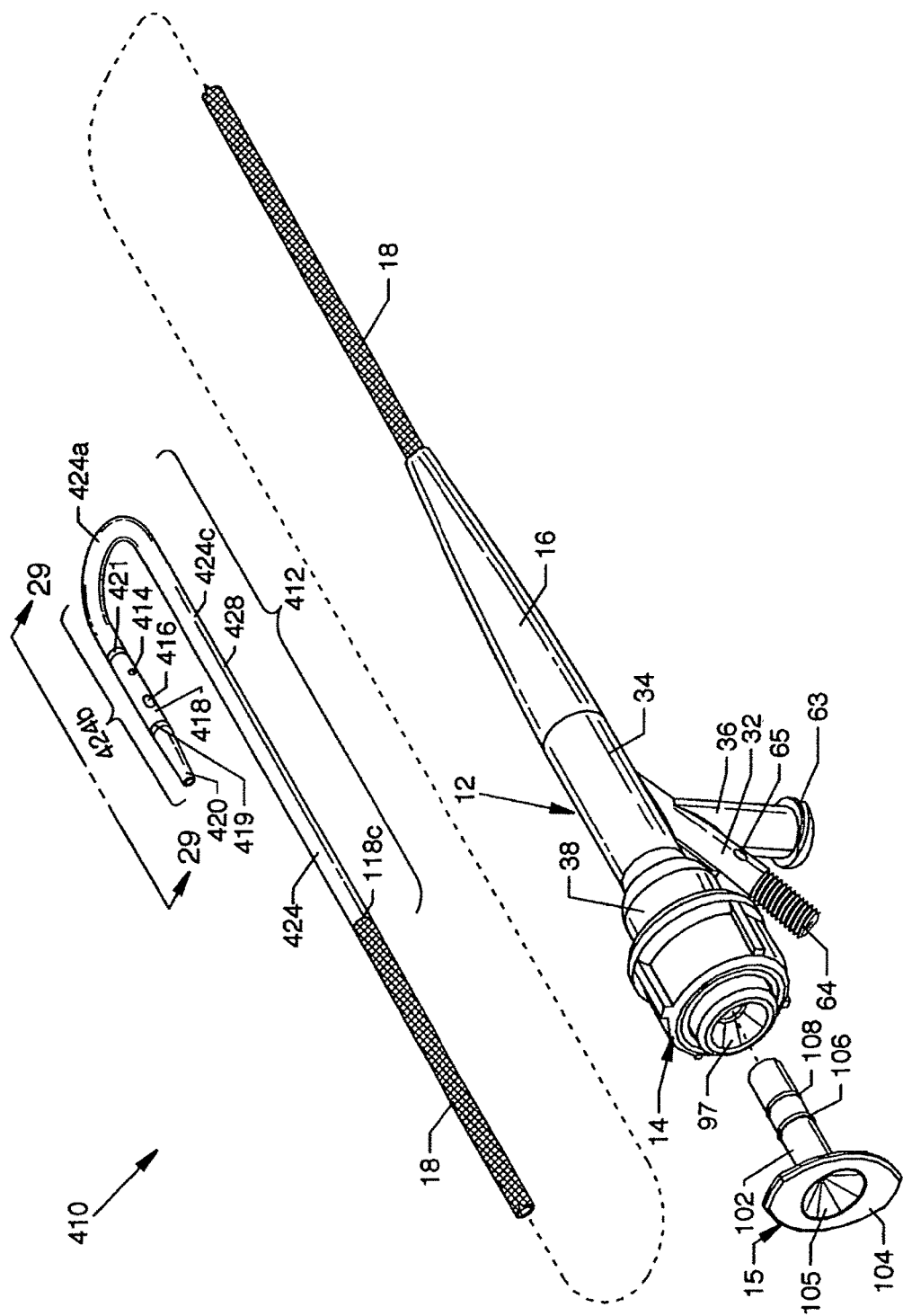
FIG. 27, a third alternative embodiment, is an isometric view of an enhanced cross stream mechanical thrombectomy catheter with backloading manifold including a smooth catheter tube which is curved.

FIG. 27, a third alternative embodiment, is an isometric view of an enhanced cross stream mechanical thrombectomy catheter with backloading manifold 410 incorporating much of the structure previously described, but differing by the substitution of a smooth catheter tube assembly 412, including a smooth catheter tube 424, which is curved approximately 180.degree, and other components and structure housed in the smooth catheter tube assembly 412 for the straight smooth catheter tube assembly 19 and previously described components and structure housed in the straight smooth catheter tube assembly 19 of the first embodiment. Also, previously described components are utilized including the components of or components attached to or associated with the centrally located backloading manifold 12 involving the hemostatic nut 14, the introducer 15, the flexible and tapered strain relief 16, and the braided catheter tube 18. The smooth catheter tube 424, which is continuous, flexible and exhibits position memory, includes a curved section 424a located between a reversed section 424b and a straight section 424c opposing the reversed section 424b. The smooth catheter tube assembly 412 is connected to and extends distally from the braided catheter tube 18 at a junction 118c and includes an outflow orifice 414 and an inflow orifice 416 each extending through the wall of the reversed section 424b of the smooth catheter tube 424 and each located in longitudinal alignment along an imaginary line at the inwardly facing aspect 418 of the reversed section 424b of the smooth catheter tube 424 and each opposingly facing the straight section 424c of the smooth catheter tube 424. Also included as part of the reversed section 424b is a distally located flexible tapered tip 420. Radiopaque marker bands 419 and 421 are located on the reversed section 424b of the smooth catheter tube 424 flanking the outflow orifice 414 and the inflow orifice 416.

Figure 28:
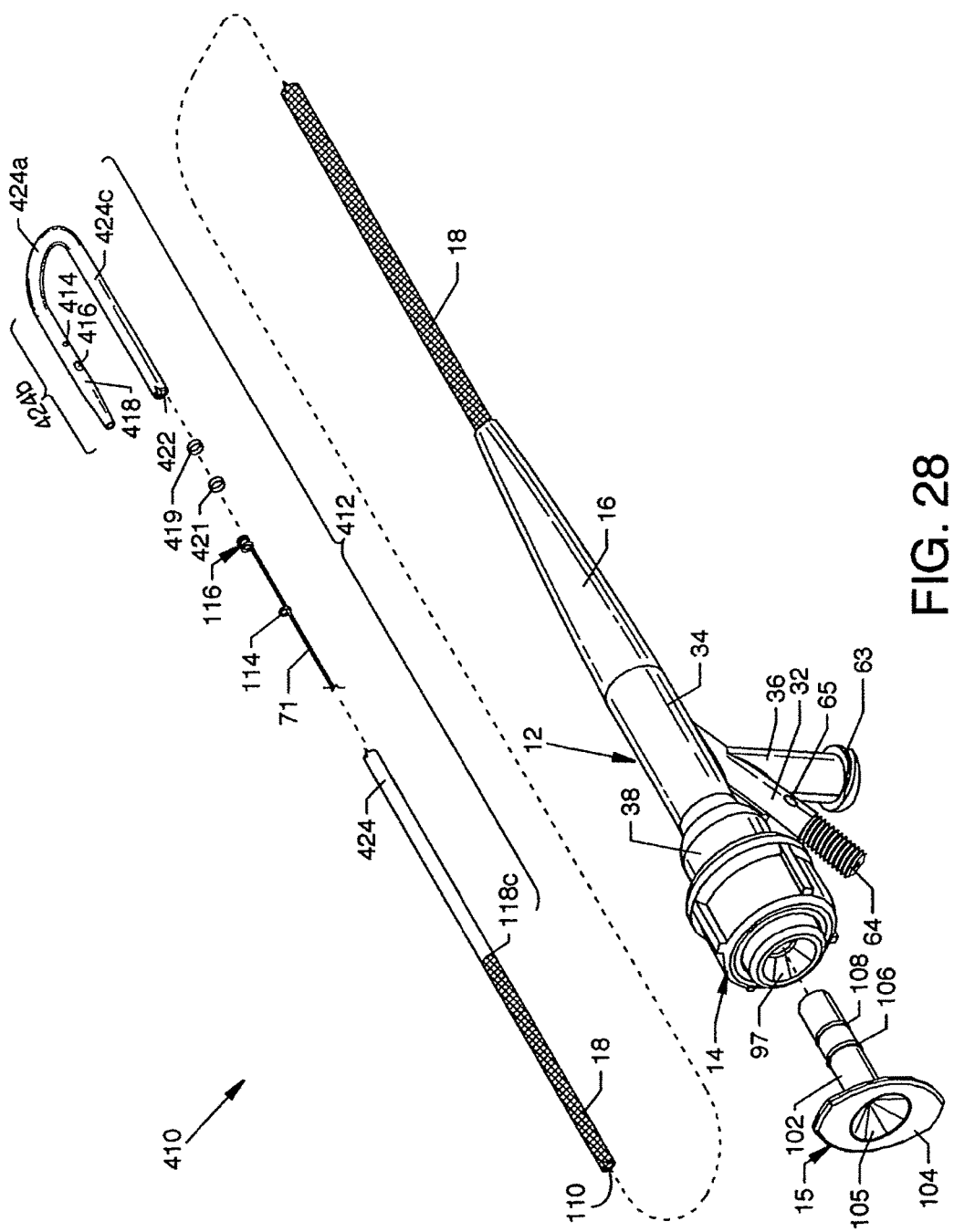
FIG. 28 is a partially exploded isometric view of the enhanced cross stream mechanical thrombectomy catheter with backloading manifold illustrated in FIG. 27.
Figure 29:
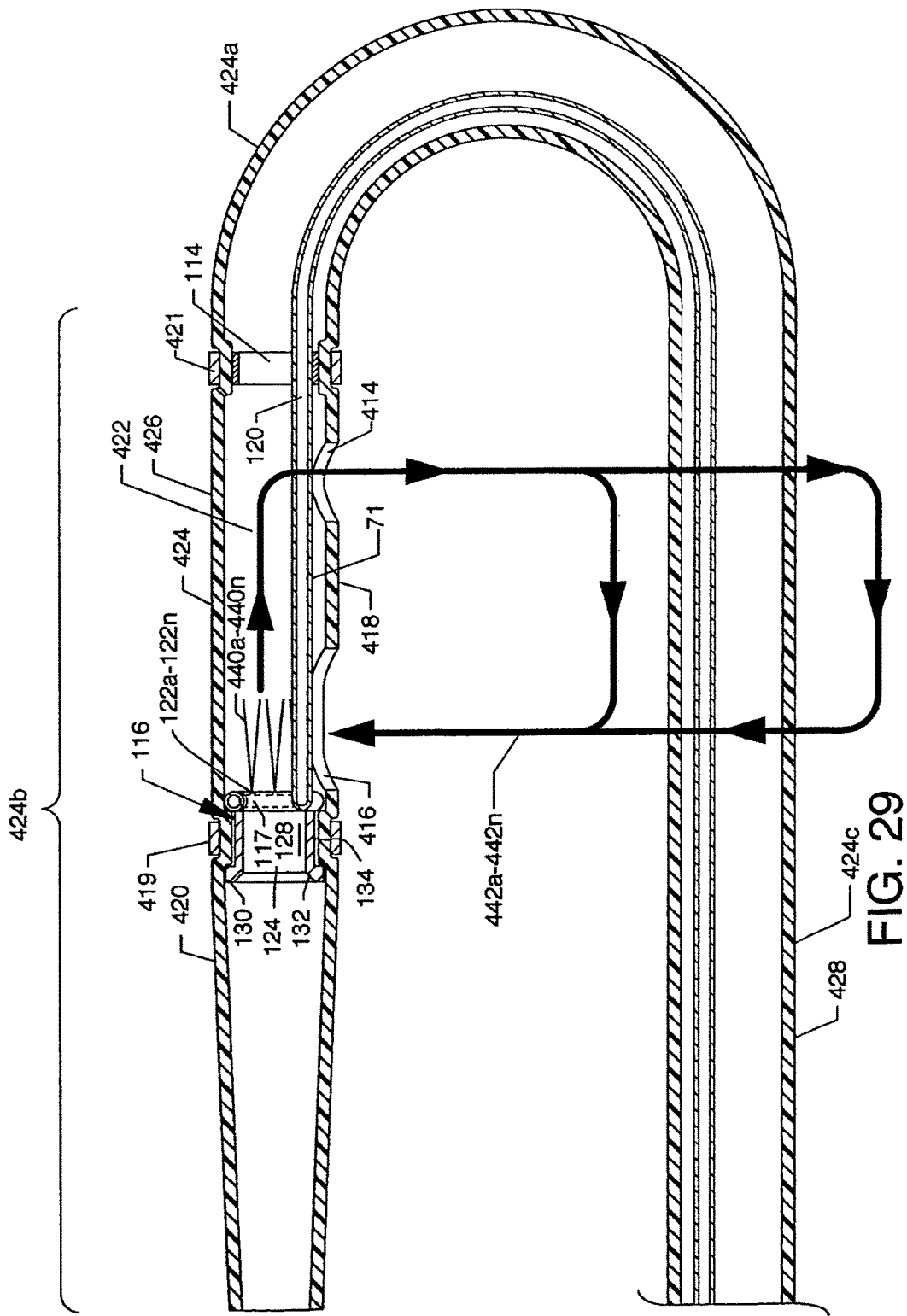
FIG. 29 is a cross section side view of the components of the distal region of the smooth catheter tube assembly along line 29-29 of FIG. 27.

FIG. 28 is a partially exploded isometric view of the enhanced cross stream mechanical thrombectomy catheter with backloading manifold 410; and FIG. 29 is a cross section side view of the components of the distal region of the smooth catheter tube assembly 412 along line 29-29 of FIG. 27. With reference to FIGS. 28 and 29, the third alternative embodiment is now further described.

The smooth catheter tube assembly 412, the components of which are depicted fully in FIGS. 27 and 28, includes a lumen 422 extending the length of the centrally located smooth catheter tube 424 including the flexible tapered tip 420, the reversed section 424b, the curved section 424a, and the straight section 424c about which and in which other components are located to connect with the lumen 110 of the braided catheter tube 18 at or near the junction 118c to the interior of the backloading manifold 12. The proximal portion of the high pressure tube 71 extends distally and through the lumen 110 of the braided catheter tube 18, and thence along the lumen 422 of and along the smooth catheter tube 424 to terminate as part of the fluid jet emanator 116, shown in FIG. 29, adjacent to the flexible tapered tip 420 at the distal end of the lumen 422 of the smooth catheter tube 424. In addition to the inwardly facing aspect 418 along the reversed section 424b, outwardly facing aspects are incorporated into the smooth catheter tube 424, including an outwardly facing aspect 426 along the outer portion of the reversed section 424b and an outwardly facing aspect 428 along the outer portion of the straight section 424c. Also shown in FIG. 27 is the junction 118c between the smooth catheter tube assembly 412 and the braided catheter tube 18, such junction being suitably effected to provide for a smooth and continuous coupling of the smooth catheter tube assembly 412 and the braided catheter tube 18.

Mode of Operation

The mode of operation of the enhanced cross stream mechanical thrombectomy catheter with backloading manifold 410 is explained with reference to FIGS. 29, 30 and 31. High velocity fluid jets 440a-440n are shown emanating proximally from the plurality of jet orifices 122a-122n of the terminated loop 117 into the lumen 422 of the smooth catheter tube 424 for subsequent creation of and culminating in cross stream jets 442a-442n, shown by heavy lines, where the high velocity fluid jets 440a-440n flow as cross stream jets 442a-442n from the outflow orifice 414 and return through the inflow orifice 416, while accomplishing ablative action with adhered blood vessel thrombus material and for maceration of foreign material in concert with the high velocity fluid jets 440a-440n. Foreign material is introduced through the inflow orifice 416 and into the lumen 422 after dislodging from a vessel wall for macerating impingement by the high velocity fluid jets 440a-440n. Macerated foreign material, i.e., thrombotic particulate, contained in the cross stream jets 442a-442n, flows through and within the lumen 422 of the smooth catheter tube 424, as also depicted by heavy lines. The cross stream jets 442a-442n, while being forcefully directed outwardly and toward the wall of the blood vessel 142 by opposite reaction, urge the distal portion of the smooth catheter tube 424 in the direction opposite the outward flow direction and away from the impingement area of the cross stream jets 442a-442n with the immediate thrombotic deposit or lesion 144 and/or the wall of the blood vessel 142, thus distancing the cross stream jets 442a-442n from the immediate thrombotic deposit or lesion 144 and/or the wall of the blood vessel 142, and thereby minimizing potential blood vessel wall damage. More specifically, the reversed section 424b can be positioned in very close proximity with or can intimately engage the inner wall of the blood vessel 142, as described later in detail. Such distancing also removes the inflow orifice 416 from close proximity with and away from the opposed wall of the blood vessel 142, thereby minimizing the chance of ingestion of the blood vessel 142 wall structure by the inflow orifice 416. The cross stream jets 442a-442n traversing between the outflow orifice 414 and the inflow orifice 416 combine to offer an enhanced broad cross section ablation area, such area having a breadth substantially larger and having more concentrated force than prior art devices using multiple inflow and outflow orifices where cross streams are of diminished force and breadth. Having a concentrated flow combining cross stream jets 442a-442n allows selective ablation to take place.

Figure 30:
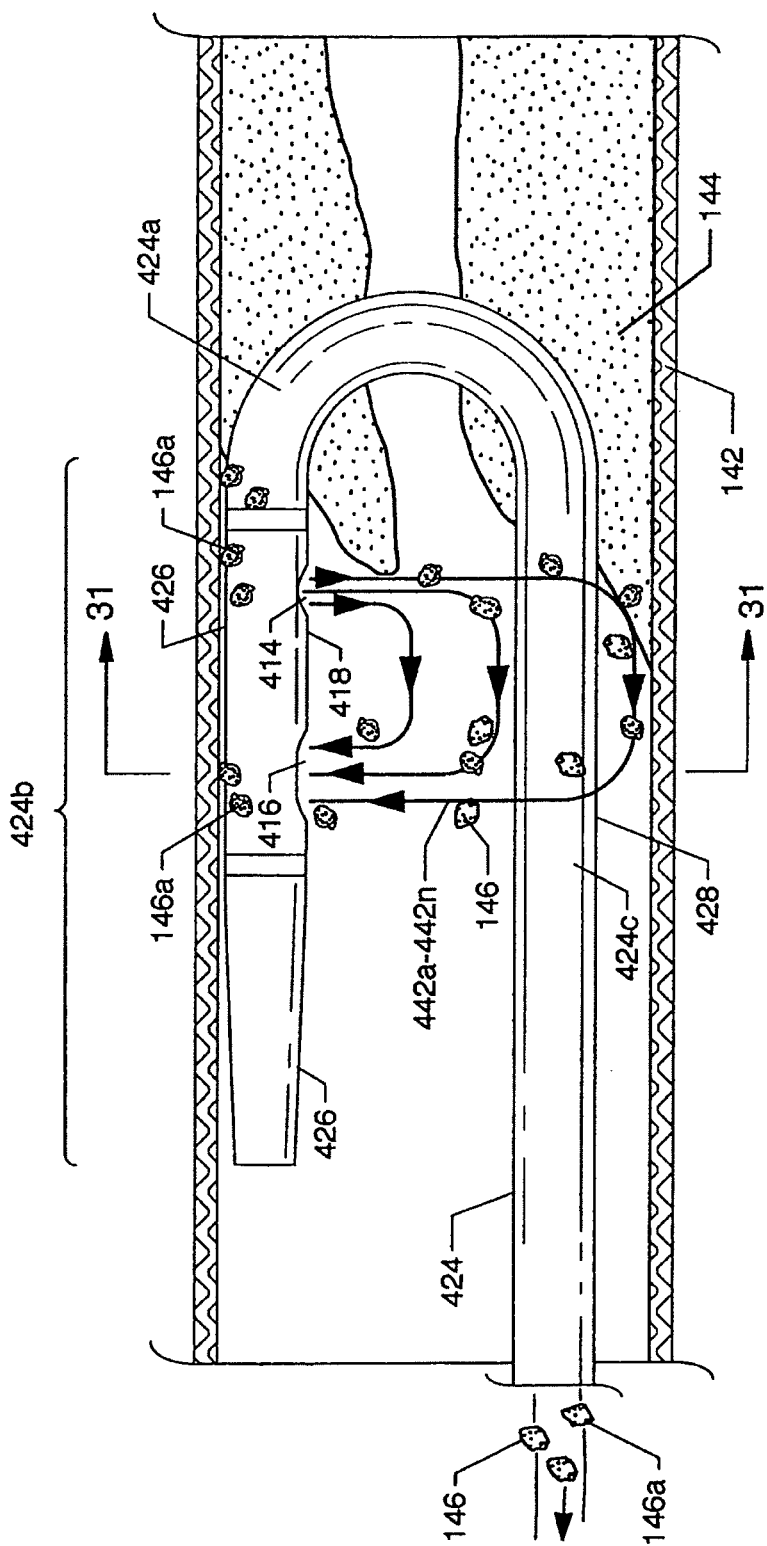
FIG. 30 is a side view of the distal region of the enhanced cross stream mechanical thrombectomy catheter with backloading manifold constituting the third alternative embodiment at a thrombus site.
Figure 31:
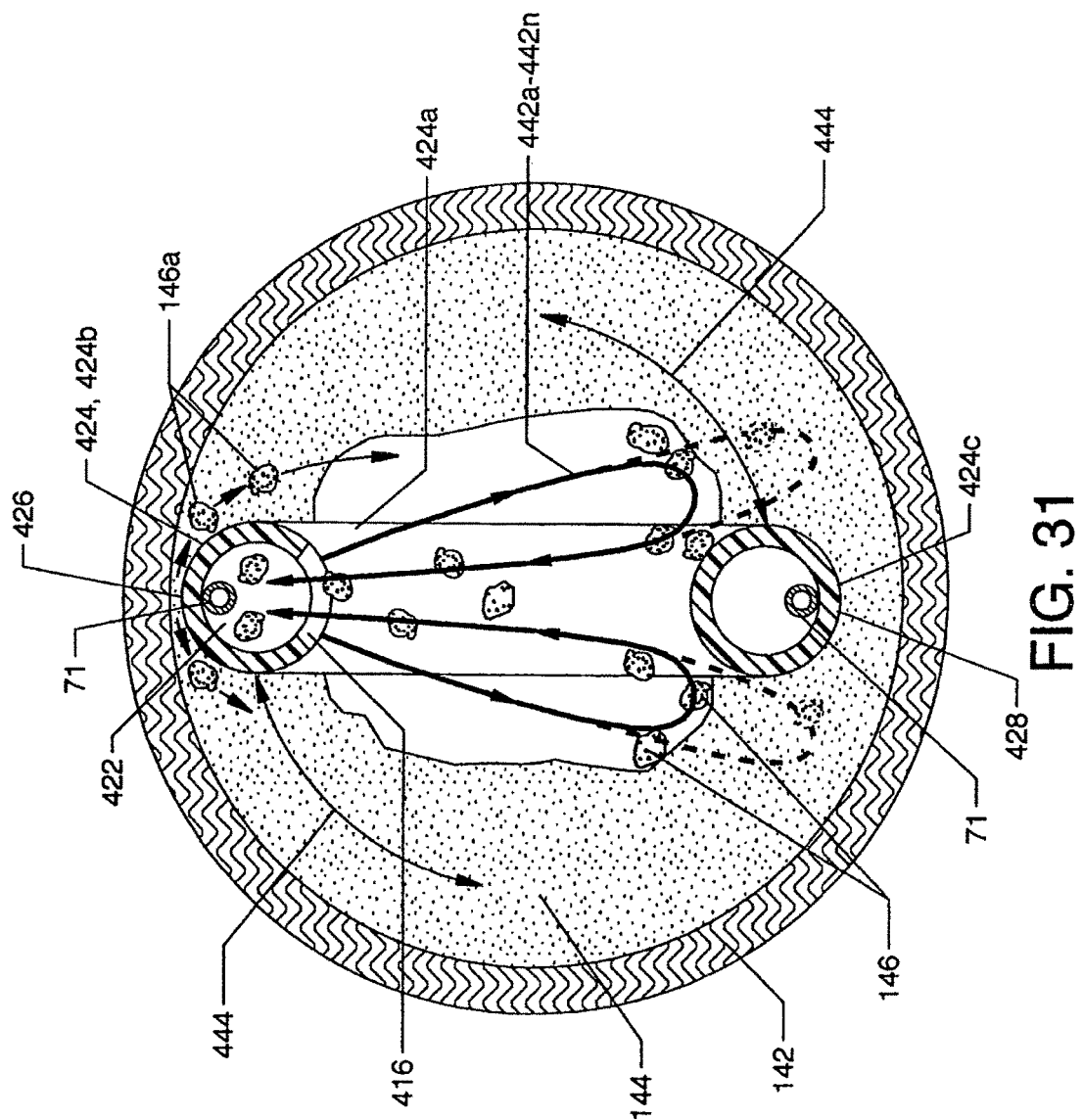
FIG. 31 is a cross section view along line 31-31 of FIG. 30.

FIG. 30 is a side view of the distal region of the enhanced cross stream mechanical thrombectomy catheter with backloading manifold 410 showing, in particular, the distal end of the smooth catheter tube 424 positioned in a blood vessel 142 (shown in cross section) at a site of a thrombotic deposit or lesion 144, and FIG. 31 is a cross section view along line 31-31 of FIG. 30 showing ablative action of the cross stream jets 442a-442n with the thrombotic deposit or lesion 144, as previously described, and additionally shows abrading or scraping action of the distal end of the smooth catheter tube 424 by intimate contact with foreign matter, such as thrombus material 144, in a blood vessel 142 which could be a large blood vessel. While FIG. 30 depicts the smooth catheter tube 424 as being in a blood vessel in particular, it is to be understood that it is not limited to use in a blood vessel, but has utility with respect to any body cavity in general. High velocity fluid jets 440a-440n (shown in FIG. 29) of saline or other suitable solution are emanated or emitted in a proximal direction from the fluid jet emanator 116 into the smooth catheter tube 424 and pass through the outflow orifice 414 creating cross stream jets 442a-442n directed toward the wall of the blood vessel 142 having thrombotic deposits or lesions 144, and thence are influenced by the low pressure at the inflow orifice 416 to cause the cross stream jets 442a-442n to be directed distally substantially parallel to the central axis of the blood vessel 142 to impinge and break up thrombotic deposits or lesions 144 and to, by entrainment, urge and carry along the dislodged and ablated thrombotic particulate 146 of the thrombotic deposits or lesions 144 through the inflow orifice 416, a relatively low pressure region, and into the lumen 422 which functions as a recycling maceration lumen or chamber. The entrainment through the inflow orifice 416 is facilitated by a low pressure source presented by the high velocity fluid jets 440a-440n. The outflow is driven by internal pressure which is created by the high velocity fluid jets 440a-440n. The enhanced clot removal is enabled because of the recirculation pattern established between inflow and outflow orifices 416 and 414, which creates a flow field that maximizes drag force on wall-adhered thrombus and because of impingement of the cross stream jets 442a-442n.

Intimate contact of or close proximity of the generally distal portion of the smooth catheter tube 424 to the inside wall of the blood vessel 142, as shown best in FIG. 31, offers yet another innovative method of thrombotic deposit or lesion 144 removal. The cross stream jets 442a-442n, while being forcefully directed outwardly and toward the wall of the blood vessel 142 during ablation activities by opposite reaction, urge the generally distal portion of the smooth catheter tube 424 in the direction opposite the outward flow direction and away from the impingement area of the cross stream jets 442a-442n with the immediate thrombotic deposit or lesion 144 and/or the wall of the blood vessel 142, thus distancing the cross stream jets 442a-442n from the immediate thrombotic deposit or lesion 144 and/or the wall of the blood vessel 142, and thereby minimizing the danger or chance of potential blood vessel wall damage or ingestion. Thus, the reversed section 424b, particularly the outwardly facing aspect 426 thereof, is forcibly maneuvered into intimate contact or into close proximity to the inside wall of the blood vessel 142, as shown in FIG. 31. Such intimate contact or close proximity to the inside wall of the blood vessel 142 is utilized to advantage by rotating the enhanced cross stream mechanical thrombectomy catheter with backloading manifold 410, particularly the smooth catheter tube 424, within the blood vessel 142, such as indicated by rotation arrows 444. Such causes scraping and abrading impingement of the reversed section 424b, especially the outwardly facing aspect 426 thereof, with the thrombotic deposit or lesion 144 at or near the inner wall of the blood vessel 142 to urge thrombotic (and lesion) particulate 146a to part from the general structure of the thrombotic deposits or lesion 144 and be entrained into the flow of the cross stream jets 442a-442n for maceration and/or evacuation through the lumen 422, as shown in FIG. 31. To and fro operation of the enhanced cross stream mechanical thrombectomy catheter with backloading manifold 410 can also be incorporated into operation of the enhanced cross stream mechanical thrombectomy catheter with backloading manifold 410 either singularly or in combination with rotation, as just described. Further, if the general distal end of the smooth catheter tube 424 is larger, or if the blood vessel is smaller, both the straight section 424c with the outwardly facing aspect 428 and the reversed section 424b with the outwardly facing aspect 426 can be utilized for rotational or for to and fro motion scraping and abrading impingement with the thrombotic deposits or lesions 144 at or near the inner wall of the blood vessel 142 to urge thrombotic (and lesion) particulate 146a to part from the general structure of the thrombotic deposits or lesion 144 to be entrained into the flow of the cross stream jets 442a-442n for maceration and/or evacuation through the lumen 422. Even more vigorous scraping and abrading could be accomplished if the general distal end of the smooth catheter tube 424 were slightly oversized with respect to the blood vessel 142.

A previously placed guidewire (not shown) is incorporated to load the enhanced cross stream mechanical thrombectomy catheter with backloading manifold 410 within the vasculature by first utilizing the distal end of the lumen 422 followed by subsequent advancement by the enhanced cross stream mechanical thrombectomy catheter with backloading manifold 410 along the guidewire in close proximity to a thrombus site. In the alternative, the first guidewire can be withdrawn completely from the enhanced cross stream mechanical thrombectomy catheter with backloading manifold 410 and swapped by backloading with another guidewire of other properties and attributes, if required. An advantage of an embodiments of the present disclosure is that the guidewire can be introduced by a front loading approach or by a backloading approach and, therefore, can be removed and reintroduced or can be replaced by a different guidewire.

The concentrated cross stream jets 442a-442n traversing between the outflow orifice 414 and the inflow orifice 416 combine to offer an enhanced broad cross section ablation area, such area having a breadth substantially larger and having more concentrated force than prior art devices using multiple inflow and outflow orifices where cross streams are of diminished force and breadth. Having a concentrated flow combining cross stream jets 442a-442n offers selective and directed ablation to take place. Prior art devices using multiple inflow and outflow orifices and having multiple flow areas generate cross streams which are equally weak in all directions, as the flow force is divided between the multiple flow streams, whereby ablation forces cannot be concentrated where desired. The distal end of the smooth catheter tube 424 can be rotated axially to direct the cross stream jets 442a-442n about a longitudinal axis to have 360.degree. coverage or can be rotated axially to offer coverage partially about the longitudinal axis, as required.

Figure 32:
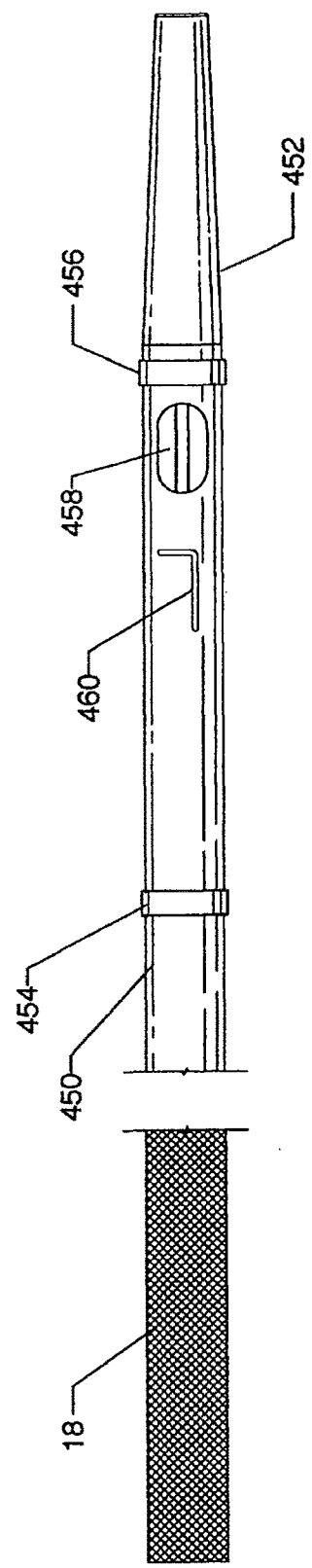
FIG. 32, a fourth alternative embodiment, is a side view of a smooth catheter tube having an alternate shape outflow orifice.

FIG. 32, a fourth alternative embodiment, is a side view of a smooth catheter tube 450 similar for the most part to and using components associated with the smooth catheter tube 20 of the first embodiment for use with an enhanced cross stream mechanical thrombectomy catheter with backloading manifold. The smooth catheter tube 450 includes a flexible tapered tip 452, an inflow orifice 458, and an outflow orifice 460, each orifice extending through the wall of the smooth catheter tube 450 where the outflow orifice takes on an L-shape to influence and shape the pattern of the cross stream jets which pass therethrough. The outflow orifice 460, as well as even the inflow orifice, could incorporate other shapes, such as, but not limited to, round, oval, elliptical, obround, tapered, slotted, rectangular, and rounded corner, or could be protruding. Radiopaque marker bands 454 and 456 are provided, as in the other embodiments.

FIG. 33, a fifth alternative embodiment, is a view of the distal portion of an alternatively provided smooth catheter tube assembly 19a incorporating the components of the smooth catheter assembly 19 shown in the first embodiment including additional outflow orifices and inflow orifices in equal and symmetric angular off-center opposition to the main outflow orifice 22 and the main inflow orifice 24.

Figure 34B:
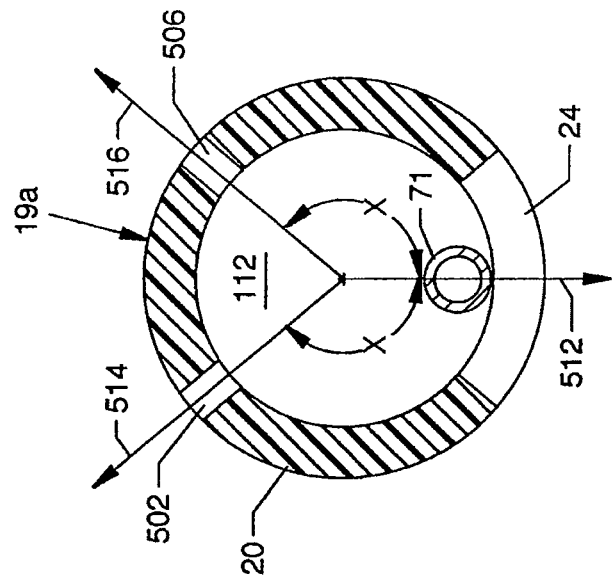
FIGS. 34a and 34b are cross section views through the outflow orifices and inflow orifices of the smooth catheter tube assembly along lines 34a-34a and 34b-34b of FIG. 33 showing cross stream jet flow regions.
Figure 34A:
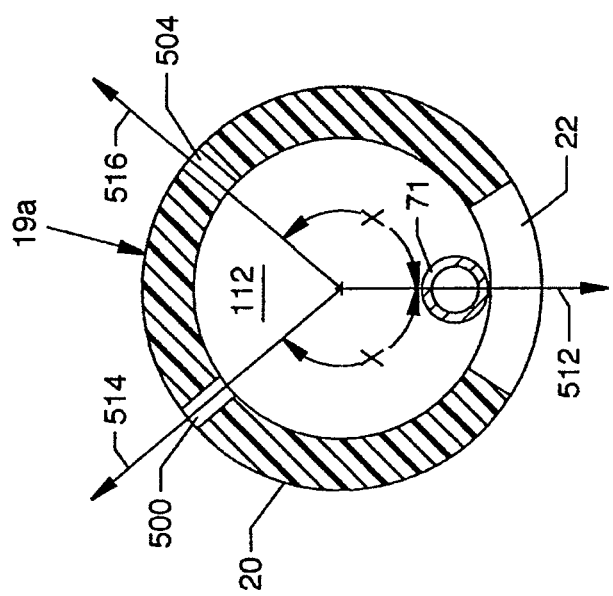

FIGS. 34a and 34b are cross section views through the outflow orifices and inflow orifices of the smooth catheter tube assembly 19a along the lines 34a-34a and 34b-34b of FIG. 33. With reference to FIGS. 33, 34a and 34b, the additional outflow and inflow orifices are now described. The additional outflow orifices 500 and 504 and inflow orifices 502 and 506, in sets, are located along imaginary lines extending longitudinally along the distal surface of the smooth catheter tube 20 and extend through the wall of the smooth catheter tube 20 where such imaginary lines preferably are parallel and offset in equiangular and symmetrical fashion from direct opposition with an imaginary line upon which the outflow orifice 22 and the inflow orifice 24 can align. Although two sets of additional outflow orifices and inflow orifices are shown, any number of sets can be incorporated as desired so long as symmetry is maintained. The sets of additional outflow orifices and inflow orifices include outflow orifices 500 and 504 and inflow orifices 502 and 506 which are smaller than outflow orifice 22 and inflow orifice 24 which, in total and in combination, produce additional cross stream jet flow, force and quantity less than that provided by the outflow orifice 22 and the inflow orifice 24. One additional set of outflow orifices and inflow orifices includes an outflow orifice 500 and an inflow orifice 502. Another additional set of outflow orifices and inflow orifices includes an outflow orifice 504 and an inflow orifice 506.

Figure 35:
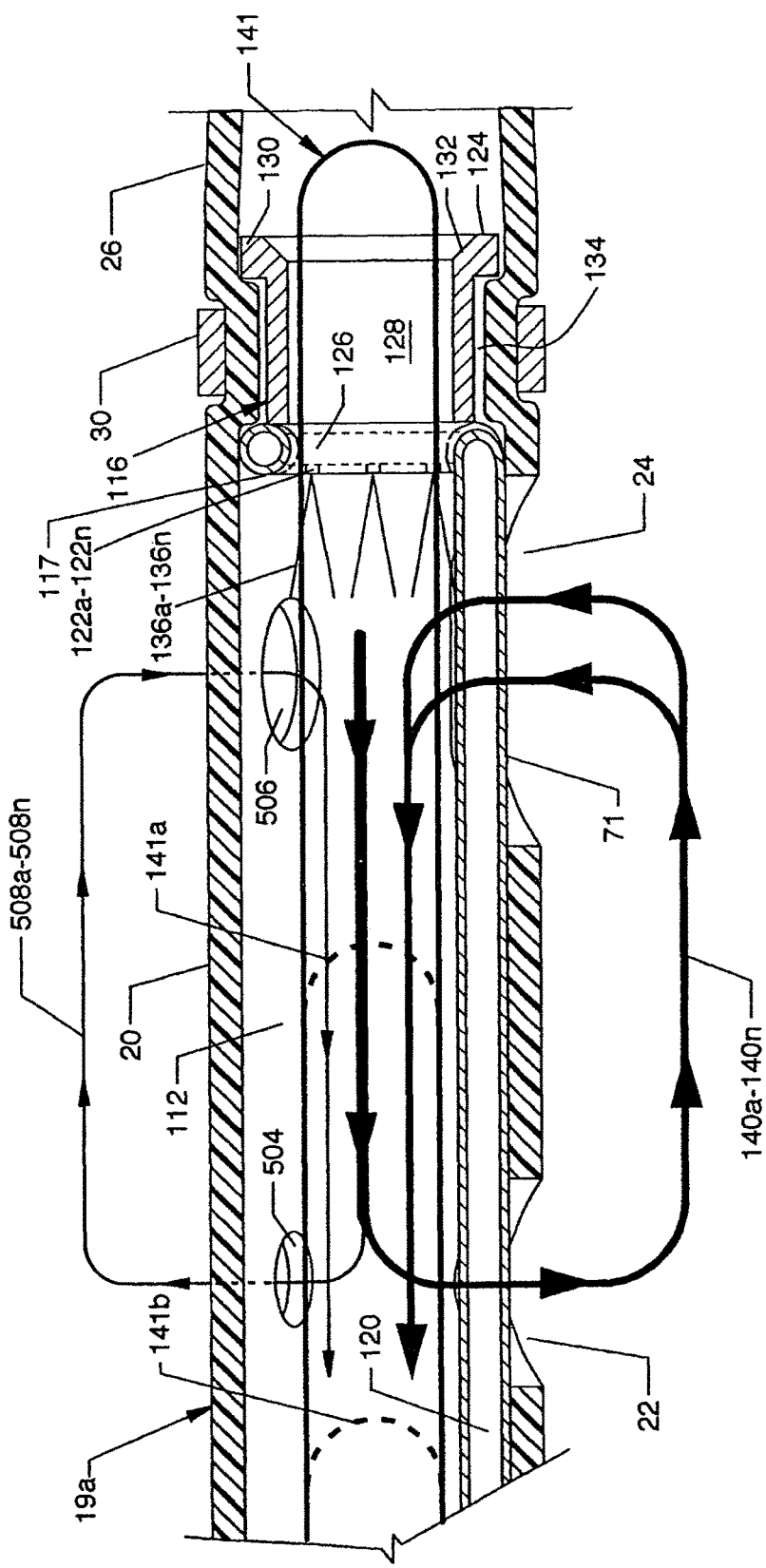
FIG. 35 is a side view in cross section like FIG. 10 wherein the distal portion of the smooth catheter tube additionally includes an outflow orifice and an inflow orifice; and, FIG. 36 is a side view of the distal region of the enhanced cross stream mechanical thrombectomy catheter with backloading manifold constituting the fifth alternative embodiment showing the distal end of the smooth catheter tube assembly positioned in a blood vessel-shown in cross section at a site of a thrombotic deposit or lesion.

FIG. 35 is a side view in cross section like FIG. 10 wherein the distal portion of the smooth catheter tube 20 additionally shows the outflow orifice 504 and the inflow orifice 506 in the structure thereof. In addition to the attributes, features and flow paths described in FIG. 10, high velocity fluid jets 136a-136n are shown emanating proximally from the plurality of jet orifices 122a-122n into the lumen 112 of the smooth catheter tube 20 for subsequent creation of and culminating in cross stream jets 508a-508n shown traveling from the outflow orifice 504 and returning through the inflow orifice 506 for entry for maceration by the high velocity fluid jets 136a-136n and/or exhausting proximally with the flow within the distal portion of the smooth catheter tube 20 as generally depicted by arrowed lines. The outflow orifice 500 and the inflow orifice 502 are incorporated into use in the same manner culminating in symmetrically disposed cross stream jets 510a-510n traveling from the outflow orifice 500 and returning through the inflow orifice 502, as shown in FIG. 36.

In addition to longitudinal alignment of the outflow orifice 500 and corresponding inflow orifice 502 and of the outflow orifice 504 and corresponding inflow orifice 506 with respect to each other and to the inflow orifice 22 and the outflow orifice 24 along imaginary lines, symmetrical alignment attributes and relationships are also addressed in the terms of cross stream jet flow region relationships as shown in FIGS. 34a and 34b. A major cross stream jet flow region 512 centers along and about the cross stream jets 140a-140n, the outflow orifice 22 and the inflow orifice 24 and substantially along the center of the lumen 112, such region being substantially perpendicular to the outflow orifice 22 and the inflow orifice 24. In a somewhat similar fashion, a minor cross stream jet flow region 514 centers along and about the cross stream jets 510a-510n (FIG. 36), the outflow orifice 500 and the inflow orifice 502 and substantially along the center of the lumen 112 such region being substantially perpendicular to the outflow orifice 500 and the inflow orifice 502. Also in a somewhat similar fashion, a minor cross stream jet flow region 516 centers along and about the cross stream jets 508a-508n, the outflow orifice 504 and the inflow orifice 506 and substantially along the center of the lumen 112, such region being substantially perpendicular to the outflow orifice 504 and the inflow orifice 506. Symmetrical angular relationships are maintained between major cross stream jet flow region 512 and each of the minor cross stream jet flow regions 514 and 516. For purposes of example and illustration, an angle X between the major cross stream jet flow region 512 and the minor cross stream jet flow region 514 corresponds to and is the same value as an angle X between the major cross stream jet flow region 512 and the minor cross stream jet flow region 516, whereby symmetry exists. The value of the angle X can be unilaterally changed during manufacturing to maintain symmetry, as just previously described. The resultant combination of symmetric but lesser flow along and about the minor cross stream jet flow regions 514 and 516 opposes the stronger flow along and about the major cross stream jet flow region 512 to assist in centering of the smooth catheter tube assembly 19a within a blood vessel, as well as offering ablation services while still allowing urging of the smooth catheter tube assembly 19a toward the periphery of a blood vessel 142.

Figure 36:
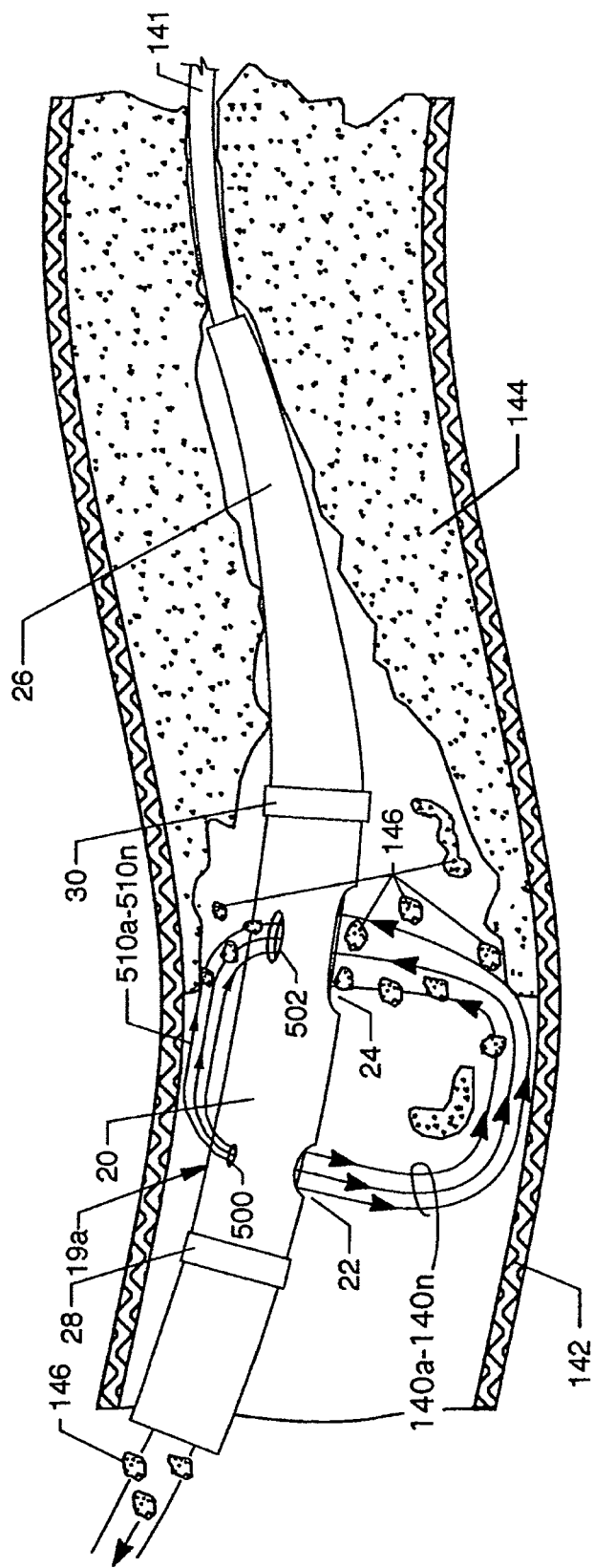

FIG. 36 is like FIG. 11 wherein a side view of the distal region of the enhanced cross stream thrombectomy catheter with backloading manifold 10 incorporating the use of the smooth catheter tube assembly 19a is shown positioned in a blood vessel 142 at a site of a thrombotic deposit or lesion 144 or other undesirable matter. In addition to and in cooperation with the mode of operation of the first embodiment, such as described with reference to FIG. 11 and associated figures, the use and features of the outflow orifice 500 and the inflow orifice 502 and of the similarly constructed and similarly functioning outflow orifice 504 and inflow orifice 506 (not shown in this FIG. 36) are described. The cross stream jets 510a-510n, which are directly related to the minor cross stream jet flow region 514 and similar to cross stream jets 508a-508n which are directly related to the minor cross stream jet flow region 516, are directed away from the main cross stream path such as provided by the cross stream jets 140a-140n which are directly related to the major cross stream jet flow region 512, to offer additional ablation and exhausting of thrombotic deposits or lesions 144 to that region where the smooth catheter tube 20 is directed and urged toward the blood vessel 144 by the more influential power of the relatively stronger cross stream jets 140a-140n. Such positional urging of the smooth catheter tube 20, as described in the first embodiment, is the dominant factor in urging of the smooth catheter tube 20 away from the wall of the blood vessel 142 near the outflow orifice 22 and the inflow orifice 24, as the flow and force therethrough is greater than that provided by such combined flow and force through the outflow orifice 500 to the inflow orifice 502 and through the outflow orifice 504 to the inflow orifice 506. The use of the outflow orifice 500 and the inflow orifice 502 and of the similarly constructed and similarly functioning outflow orifice 504 and the inflow orifice 506 provides for more complete ablation and exhausting while still allowing urging of the smooth catheter tube 20 towards the side of the blood vessel 142 opposite the greater ablation activity. Symmetry of the cross stream jet flows is provided by the equiangular offset of the outflow orifice 500 and the inflow orifice 502 and of the similarly constructed and similarly functioning outflow orifice 504 and the inflow orifice 506 with respect to the cross stream jet flow provided by the outflow orifice 22 and the inflow orifice 24. Such symmetry ensures stability of the smooth catheter tube assembly 19a during ablation procedures.

Various modifications can be made to the present disclosure without departing from the apparent scope thereof.

It is claimed:

1. A medical device, comprising:
an elongate tubular member, wherein the tubular member includes a proximal portion, a distal portion and a preformed curved portion positioned between the distal and proximal portions, and wherein the distal portion points in a proximal direction from the curved portion to a distal tip;
a high pressure tube extending within a lumen of the tubular member; and
a fluid jet emanator coupled to the high pressure tube, the fluid jet emanator having at least one jet orifice for directing fluid proximally through the lumen of the tubular member; and
wherein the curved portion of the elongate tubular member is configured to position the distal portion in a double-back configuration in a body lumen.

2. The medical device of claim 1, further comprising an outflow orifice located on the distal portion of the tubular member, wherein the outflow orifice is configured to generate a fluid jet stream out of the lumen of the tubular member.

3. The medical device of claim 2, further comprising an inflow orifice located on the distal portion of the tubular member, wherein the inflow orifice is configured to receive the fluid jet stream generated by the outflow orifice.

4. The medical device of claim 3, wherein the inflow orifice is positioned distally of the outflow orifice along the tubular member.

5. The medical device of claim 4, wherein the outflow orifice and the inflow orifice are located at discrete locations along the tubular member, and wherein a continuous surface extends along the tubular member at a location opposed to the discrete locations of the outflow and inflow orifices.

6. The medical device of claim 5, wherein the at least one fluid jet is directed proximally from the emanator toward the outflow orifice.

7. The medical device of claim 6, wherein the outflow orifice and the inflow orifice are aligned on one side of the tubular member.

8. The medical device of claim 7, wherein the fluid jet stream comprises two or more fluid flow paths directed out of the lumen of the tubular member via the outflow orifice and into the lumen of the tubular member via the inflow orifice.

9. The medical device of claim 7, wherein the fluid jet stream is configured to position the continuous surface extending along the tubular member against an inner surface of a body lumen.

10. The medical device of claim 7, wherein the fluid jet stream is recirculated between the outflow orifice and the inflow orifice.

11. The medical device of claim 7, wherein the recirculated fluid jet stream defines an entrainment fluid jet stream, wherein the entrainment circuit is configured to entrain particulate and macerate particulate therein.

12. The medical device of claim 1, wherein the curved portion of the tubular member curves such that the distal portion of the tubular member and the proximal portion of the tubular member are substantially parallel and opposed to one another.

13. A thrombectomy catheter, comprising:
an elongate tubular member, wherein the tubular member includes a proximal portion, a distal portion and a preformed curved portion positioned between the distal and proximal portions, and wherein the distal portion points in a proximal direction from the curved portion to a distal tip, and wherein the tubular member includes an outflow orifice and an inflow orifice;

a high pressure tube extending within a lumen of the tubular member; and a fluid jet emanator coupled to the high pressure tube, the fluid jet emanatory directing at least one fluid jet out of the lumen of the tubular member via the outflow orifice and into the lumen of the tubular member via the inflow orifice, and wherein the curved portion of the elongate tubular member is configured to position the distal portion in a double-back configuration in a body lumen.

14. The thrombectomy catheter of claim 13, wherein the inflow orifice is positioned distally of the outflow orifice along the tubular member.

15. The thrombectomy catheter of claim 13, wherein the curved portion of the tubular member curves such that the distal portion of the tubular member and the proximal portion of the tubular member are substantially parallel to one another.

16. The thrombectomy catheter of claim 13, wherein fluid jet further comprises a fluid jet stream, and wherein the fluid jet stream defines a fluid jet path that recirculates between the outflow and inflow orifices.

17. The thrombectomy catheter of claim 16, wherein the fluid jet stream includes two or more fluid jet paths.

18. The thrombectomy catheter of claim 16, wherein the recirculated fluid jet path is configured to entrain particulate and macerate particulate therein.

19. A thrombectomy catheter, comprising;

an elongate tubular member having a lumen extending therein, wherein the tubular member includes a proximal portion, a distal portion and a preformed curved portion positioned between the distal and proximal portions, and wherein the distal portion points in a proximal direction from the curved portion to a distal tip, and wherein the tubular member includes an outflow orifice and an inflow orifice;

wherein the distal portion is configured to recirculate a fluid jet stream around an entrainment fluid circuit; and wherein the entrainment fluid circuit passes through the outflow orifice, the inflow orifice and the catheter lumen, and wherein the curved portion of the elongate tubular member is configured to position the distal portion in a double-back configuration in a body lumen.

20. The thrombectomy catheter of claim 19, wherein the inflow orifice is positioned distally of the outflow orifice along the tubular member.

* * * * *